United States Patent
De Vivo et al.

(10) Patent No.: US 11,198,682 B2
(45) Date of Patent: Dec. 14, 2021

(54) SUBSTITUTED PYRIMIDINES AS INHIBITORS FOR A RHO FAMILY OF GTP-ASES

(71) Applicants: Fondazione Istituto Italiano Di Tecnologia, Genoa (IT); The Regents of the University of California, Oakland, CA (US)

(72) Inventors: Marco De Vivo, Genoa (IT); Anand Ganesan, Irvine, CA (US); Jose Antonio Ortega Martinez, Genoa (IT); Sohail Jahid, Irvine, CA (US)

(73) Assignees: Fondazione Istituto Italiano Di Tecnologia, Genoa (IT); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/609,720

(22) PCT Filed: May 2, 2018

(86) PCT No.: PCT/IB2018/053047
§ 371 (c)(1),
(2) Date: Oct. 30, 2019

(87) PCT Pub. No.: WO2018/203256
PCT Pub. Date: Nov. 8, 2018

(65) Prior Publication Data
US 2020/0062733 A1 Feb. 27, 2020

(30) Foreign Application Priority Data
May 2, 2017 (IT) .................. 102017000047189

(51) Int. Cl.
A61K 31/505 (2006.01)
C07D 239/42 (2006.01)
C07D 401/14 (2006.01)
C07D 405/04 (2006.01)
A61K 45/06 (2006.01)

(52) U.S. Cl.
CPC ......... C07D 401/14 (2013.01); C07D 405/04 (2013.01); A61K 45/06 (2013.01)

(58) Field of Classification Search
CPC ........................... A61K 31/505; C07D 239/42
USPC .......................................... 514/256; 544/326
See application file for complete search history.

(56) References Cited

FOREIGN PATENT DOCUMENTS

| CN | 110799505 A | 2/2020 |
|---|---|---|
| CN | 112279833 A | 1/2021 |
| EP | 3619202 A1 | 3/2020 |
| IT | 201700047189 A1 | 11/2018 |
| JP | 2020-518595 A | 6/2020 |
| KR | 1020200015515 A | 2/2020 |
| SG | 11201910053 Y | 11/2019 |
| WO | 2004048365 A1 | 6/2004 |
| WO | 2018203256 A1 | 11/2018 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Jordan, V. C. Nature Reviews: Drug Discovery, 2, 2003, 205.*
Hackam, et al. JAMA, 296(14), 2006, 1731-1732.*
International Preliminary Report on Patentability for International Application No. PCT/IB2018/053047, Report dated Nov. 2019, dated Nov. 14, 2019, 8 Pgs.
International Search Report and Written Opinion for International Application No. PCT/IB2018/053047, Search completed Jun. 7, 2018, dated Jun. 21, 2018, 12 Pgs.
"Database Registry", Chemical Abstracts Service, 2012, XP002774925, Database Accession No. 1381619-32-4.
"Database Registry", Chemical Abstracts Service, 2012, XP002774926, Database Accession No. 1381324-63-5.
"Database Registry", Chemical Abstracts Service, 2013, XP002774924, Database Accession No. 1442113-78-1.
Extended European Search Report for European Application No. 20217990.9, Search completed Feb. 3, 2021, dated Feb. 12, 2021, 9 Pgs.

* cited by examiner

Primary Examiner — Douglas M Willis
(74) Attorney, Agent, or Firm — KPPB LLP

(57) ABSTRACT

The present invention relates to compounds of Formula (I) or pharmaceutically acceptable salts or solvates thereof:

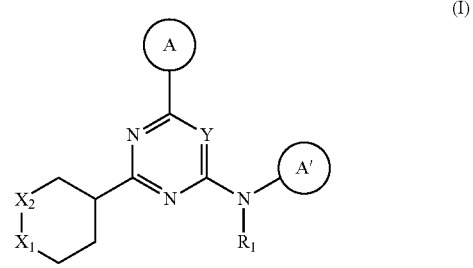

(I)

It further discloses a pharmaceutical composition comprising the compounds of Formula (I) and their uses, in particular in the treatment of diseases or disorders associated to increased relative to physiological or desired RhoJ/Cdc42 levels of expression or function.

20 Claims, 2 Drawing Sheets

SUBSTITUTED PYRIMIDINES AS INHIBITORS FOR A RHO FAMILY OF GTP-ASES

STATEMENT OF FEDERAL SUPPORT

This invention was made with government support under Grant No. 5R01CA151513-05 awarded by the Department of Health and Human Services (DHHS). The government has certain rights in the invention.

CROSS-REFERENCE TO RELATED APPLICATIONS

The present application is a U.S. national stage of PCT Application No. PCT/IB2018/053047, entitled "TRISUB-STITUTED PYRIMIDINE COMPOUNDS AND COMPOSITIONS FOR THE TREATMENT OF CANCER, RETINAL DISORDERS, AND CARDIOMYOPATHIES" to De Vivo et al., filed May 2, 2018, which application claims priority to Italian Patent Application No. 102017000047189 filed May 2, 2017, the disclosures of which are incorporated herein by reference in their entireties.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

FIELD OF THE INVENTION

The present invention relates to novel RhoJ inhibitors for the treatment of cardiomyopathies, retinal disorders and cancers, in particular melanoma.

BACKGROUND OF THE INVENTION

The incidence of melanoma, a type of cancer that develops from the malignant transformation of melanocytes, is increasing while, unfortunately, traditional therapies such as dacarbazine and high-dose of interleukin-2 (IL-2) chemotherapies are cytotoxic and have poor efficacy, which reinforce the need for new therapeutic approaches.

More recent strategies include the use of BRAF inhibitors, such as vemurafenib. Also, immunotherapeutic approaches using antibodies blocking immune checkpoint molecules, such as ipilimumab, that targets the anti-cytotoxic T lymphocyte antigen 4 (CTLA-4), are currently used to treat unresectable melanoma. Additional studies use a combination of PD1 inhibitors, such as nivolumab, with ipilimumab. While these therapies can cause dramatic response in some patients, only 30% of patients respond to these therapies. Improved therapies are particularly needed for early stage disease, where only interleukin 2 and oncolytic viral therapies have been used with very limited success.

In this context, an alternative and promising approach is the combination of therapies where multiple agents and traditional anticancer modalities (radiation, chemotherapy or surgery) are used together to enhance treatment efficacy and reduce side effects.

All these possible therapeutic strategies, however, have not resulted in a significant decline in the mortality of melanoma patients and progression of metastatic melanoma. Intrinsic and/or acquired resistance to chemotherapies remains a major issue and generates a strong need to identify new pathways to treat it. In addition, identifying agents that have limited toxicity and could be used to treat early stage disease (stage III) would have significant therapeutic applicability.

RhoJ is currently presented as a validated target in the combined treatments strategy since its expression modulates the development of melanoma. RhoJ is a member of the Rho-family of small GTPases, known to bind and activate PAK kinases. Functional validation studies revealed that RhoJ activates PAK1, which then inhibits p53 signaling and apoptosis pathways in melanoma cells in vitro.

Additional studies showed that RhoJ and PAK1 also modulate melanoma cell migration and invasion in vitro, as well as tumor growth and invasion in melanoma xenograft model. While RhoJ was known to have a role in endothelial cell biology and angiogenesis, it was not known whether RhoJ had cell autonomous effects on the growth of melanocytic tumors. Recent studies have determined that RhoJ modulates the growth and development of melanoma tumors in autochthonous mouse models and is expressed at a higher level in stage III as compared to stage IV melanomas. Overall, these in vitro and in vivo studies revealed that RhoJ and PAK1 accelerate the growth of nascent melanoma tumors, inhibit apoptosis, and stimulate angiogenesis. Recent studies indicated that RhoJ operates in tumor cells to inhibit apoptosis by blocking the phosphorylation of BAD, which prevents BAD from inducing apoptosis. RhoJ interaction inhibitors blocked PAK kinase induced BAD phosphorylation, a similar effect to what was observed with PAK inhibitors.

Furthermore, RhoJ is also considered to play a central role in the pathophysiology of cardiomyopathies, such as Dilated CardioMyopathies (DCM) and a possible therapeutic target to specifically manipulate endothelial filopodia projections.

For these reasons blocking RhoJ can be considered a useful tool to treat pathologies such as cardiomyopathies, retinal disorders, stage III or stage IV melanomas, and other cancers which show resistance to other therapies.

Accordingly, there is a need for novel compounds to inhibit RhoJ.

BRIEF SUMMARY OF THE INVENTION

The aim of the present invention is to provide novel compounds acting as RhoJ inhibitors.

The aforementioned objective has been met according to compounds of claim 1, to a pharmaceutical composition of claim 7, to the uses of claims 10, 11 and 12. Preferred embodiments are set out within the dependent claims.

BRIEF DESCRIPTION OF THE SEVERAL VIEWS OF THE DRAWINGS

The present invention will now be described in detail with reference to the annexed drawings, wherein.

DETAILED DESCRIPTION OF THE INVENTION

Figure 1:
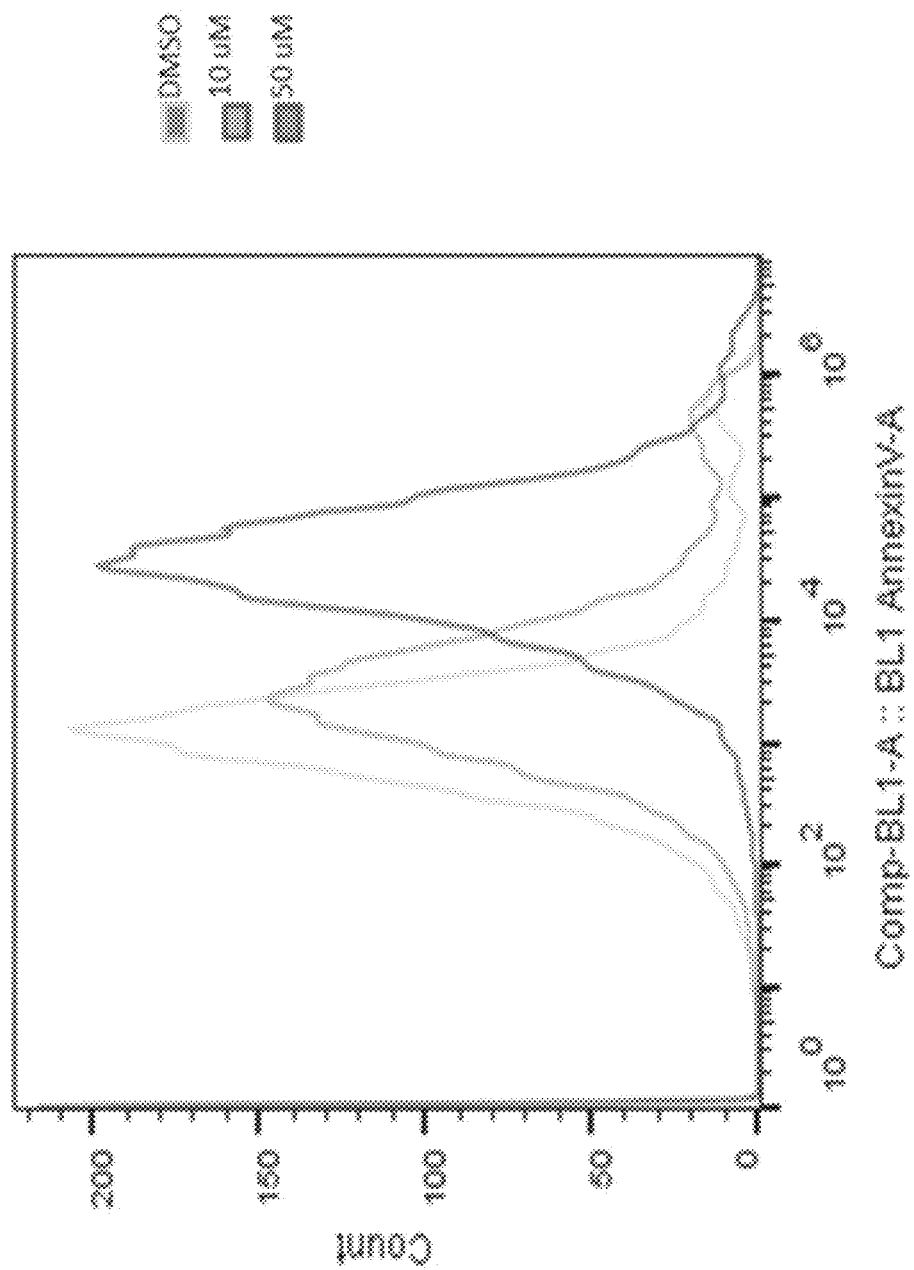
FIG. 1 illustrates apoptosis induced in WM3248 melanoma cells by RhoJ interaction inhibitor ARN12405 (compound 1) measured by flow cytometry using AnnexinV and PI.

The following paragraphs provide definitions of the various chemical moieties of the compounds according to the invention and are intended to apply uniformly throughout the specification and claims unless an otherwise expressly set out definition provides a broader definition.

The term "alkyl", as used herein by itself or as a part of another substituent, refers to aliphatic hydrocarbon groups. Such term includes linear (unbranched) chains or branched chains, which may be fully saturated, mono- or polyunsaturated.

The term "unsaturated" aliphatic hydrocarbon group encompasses alkenyl and alkynyl.

The term "alkenyl", as used herein, refers to alkyl groups, preferably having from 2 to 6 carbon atoms and containing at least one carbon-carbon double bond.

The term "alkynyl", as used herein, refers to alkyl groups, preferably having from 2 to 6 carbon atoms and containing at least one carbon-carbon triple bond.

Non-limiting examples of alkyl groups according to the invention are, for example, methyl, ethyl, propyl, isopropyl, n-butyl, iso-butyl, tert-butyl, n-pentyl, iso-pentyl, n-hexyl, ethenyl, 1-propenyl, 2-propenyl, 1- or 2-butenyl, ethynyl, 1-propynyl, 2-propynyl, 1- or 2-butynyl and the like.

The term "alkoxy", as used herein, refers to an alkyl group that is linked to the remainder of the compound by an oxygen atom.

The term "halogen", as used herein, refers to fluorine, chlorine, bromine and iodine.

The term "aromatic ring", as used herein, refers to a moiety wherein the constituent carbon atoms make up an unsaturated ring system, all atoms in the ring system are $sp^2$ hybridized and the total number of n-electrons is equal to 4n+2, wherein n is an integer.

The term "heteroaromatic ring", as used herein, refers to an aromatic ring as defined above wherein one to four carbon atoms are independently replaced by heteroatoms chosen from the group consisting of nitrogen, oxygen and sulphur. Non-limiting examples of heteroaromatic ring groups are, for example, pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl.

Unless otherwise indicated, the term "substituted", as used herein, means that one or more hydrogen atoms of the above mentioned groups are replaced with another non-hydrogen atom or functional group, provided that normal valencies are maintained and that the substitution results in a stable compound.

The term "pharmaceutically acceptable salts" refers to salts of the below identified compounds of Formula (I) that retain the desired biological activity and are accepted by regulatory authorities.

As used herein, the term "salt" refers to any salt of a compound according to the present invention prepared from an inorganic or organic acid or base and internally formed salts. Typically, such salts have a physiologically acceptable anion or cation.

Furthermore, the compounds of Formula (I) may form an acid addition salt or a salt with a base, depending on the kind of the substituents, and these salts are included in the present invention, as long as they are pharmaceutically acceptable salts.

Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, trifluoroacetic acid, oxalic acid, tartaric acid, succinic acid, malic acid, fumaric acid, maleic acid, ascorbic acid, benzoic acid, alginic acid, polyglutamic acid and naphthalene sulfonic acid.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I) may readily be isolated in association with solvent molecules by crystallization or evaporation of an appropriate solvent to give the corresponding solvates.

The compounds of Formula (I) may be in crystalline form. In certain embodiments, the crystalline forms of the compounds of Formula (I) are polymorphs.

The subject invention also includes isotopically-labelled compounds, which are identical to those recited in Formula (I) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, phosphorous, sulfur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e. $^3H$, and carbon-14, i.e. $^{14}C$, isotopes are particularly preferred for their ease of preparation and detectability. $^{11}C$ and $^{18}F$ isotopes are particularly useful in PET (Positron Emission Tomography), and $^{125}I$ isotopes are particularly useful in SPECT (Single Photon Emission Computerized Tomography), all useful in brain imaging. Furthermore, substitution with heavier isotopes such as deuterium, i.e. 2H, can afford certain therapeutic advantages resulting from greater metabolic stability, for example increased in vivo half-life or reduced dosage requirements and, hence, may be preferred in some circumstances. Isotopically-labelled compounds of Formula (I) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I) may have asymmetric carbon atoms or axial asymmetries in some cases and, correspondingly, they may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (I) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

According to a first aspect of the invention, compounds of Formula (I):

(I)

or pharmaceutically acceptable salts or solvates thereof are provided.

In the compounds of Formula (I):

$X_1$ and $X_2$ are independently selected from the group consisting of $CH_2$, $NR_2$ and O provided that $X_1$ and $X_2$ are not both $NR_2$, both O or $NR_2$ and O at the same time;

Y is selected from the group consisting of CH and N;

A and A' are independently selected from the group consisting of a 6-membered heteroaromatic ring that contains 1 or 2 nitrogen atoms and a 6-membered aromatic ring optionally substituted at any position with a substituent selected from the group consisting of $C_{1-6}$alkyl, halogen, halo-$C_{1-6}$alkyl, hydroxyl, alkoxy-$C_{1-6}$alkyl, amino, amino-$C_{1-6}$alkyl and amino-di$C_{1-6}$alkyl;

$R_1$ is selected from the group consisting of hydrogen and $C_{1-6}$alkyl;

$R_2$ is selected from the group consisting of hydrogen, $C_{1-6}$alkyl, $C_{1-6}$alkyl-alkoxy, CO—$C_{1-6}$alkyl and CO—$C_{1-6}$alkyl-alkoxy.

According to a First Embodiment

A and A' are independently selected from the group consisting of an 6-membered heteroaromatic ring that contains 1 nitrogen atom and a 6-membered aromatic ring optionally substituted at any position with a substituent selected from the group consisting of halogen, alkoxy-$C_{1-6}$alkyl, amino, amino-$C_{1-6}$alkyl, amino-di$C_{1-6}$alkyl;

$R_1$ is hydrogen;

$R_2$ is hydrogen.

According to a Second Embodiment $X_1$ is selected from the group consisting of $CH_2$, NH and O;

$X_2$ is selected from the group consisting of $CH_2$ and NH provided that $X_1$ and $X_2$ are not N at the same time;

Y is $CH_2$;

A is selected from the group consisting of 6-membered heteroaromatic ring that contains 1 nitrogen atom in position 2 or 3 and a 6-membered aromatic ring optionally substituted with a substituent selected from the group consisting of halogen and alkoxy-$C_{1-3}$alkyl;

A' is selected from the group consisting of 6-membered aromatic ring optionally substituted in meta or para positions with a substituent selected from the group consisting of halogen, alkoxy-$C_{1-6}$alkyl and amino-di$C_{1-6}$alkyl;

$R_1$ is hydrogen;

$R_2$ is hydrogen.

In a further embodiment, A is selected from the group consisting of an heteroaromatic 6-membered ring that contains 1 nitrogen atom and an unsubstituted 6-membered aromatic ring.

In a preferred embodiment, A' is a 6-membered aromatic ring substituted in para or meta position with a substituent selected from the group consisting of methoxy or an amino-di-$C_1$alkyl.

According to a third embodiment of the invention, the compounds of Formula (I) can be selected from the group consisting of:

| Compound number | Structure |
|---|---|
| 1 (ARN12405) | 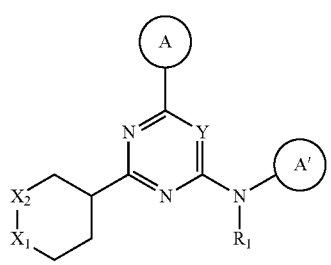 |

| Compound number | Structure |
|---|---|
| 2 | 2-(piperidin-3-yl)-6-(pyridin-3-yl)-N-(4-chlorophenyl)pyrimidin-4-amine |
| 3 | 2-(piperidin-3-yl)-6-(pyridin-2-yl)-N-(4-chlorophenyl)pyrimidin-4-amine |
| 4 | 2-(piperidin-3-yl)-6-phenyl-N-(4-chlorophenyl)pyrimidin-4-amine |
| 5 | 2-(piperidin-3-yl)-6-(pyridin-4-yl)-N-(3-chlorophenyl)pyrimidin-4-amine |
| 6 | 2-(piperidin-3-yl)-6-(4-methoxyphenyl)-N-(4-chlorophenyl)pyrimidin-4-amine |
| 7 | 2-(piperidin-3-yl)-6-(4-fluorophenyl)-N-phenylpyrimidin-4-amine |
| 8 | 2-(piperidin-3-yl)-6-phenyl-N-(4-dimethylaminophenyl)pyrimidin-4-amine |
| 9 | 2-(piperidin-3-yl)-6-phenyl-N-(4-methoxyphenyl)pyrimidin-4-amine |
| 10 | 2-(piperidin-3-yl)-6-phenyl-N-(3-dimethylaminophenyl)pyrimidin-4-amine |
| 11 | 2-(piperidin-3-yl)-6-phenyl-N-(3-methoxyphenyl)pyrimidin-4-amine |

-continued

| Compound number | Structure |
|---|---|
| 12 | 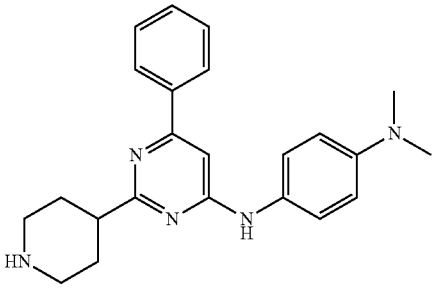 [SMILES: CN(C)c1ccc(Nc2cc(-c3ccccc3)nc(C3CCNCC3)n2)cc1] |
| 13 | 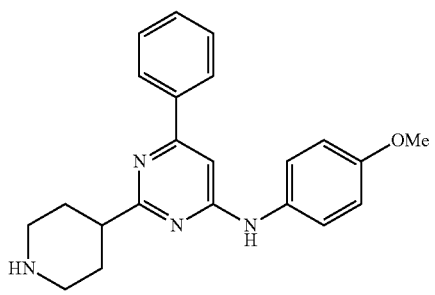 [SMILES: COc1ccc(Nc2cc(-c3ccccc3)nc(C3CCNCC3)n2)cc1] |
| 14 | 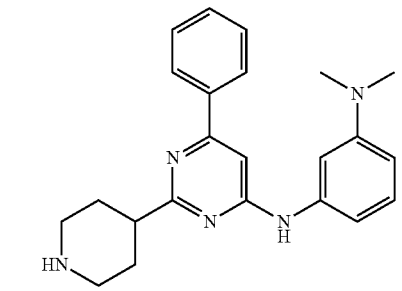 [SMILES: CN(C)c1cccc(Nc2cc(-c3ccccc3)nc(C3CCNCC3)n2)c1] |
| 15 | 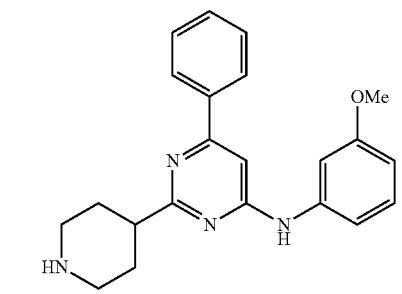 [SMILES: COc1cccc(Nc2cc(-c3ccccc3)nc(C3CCNCC3)n2)c1] |
| 16 | 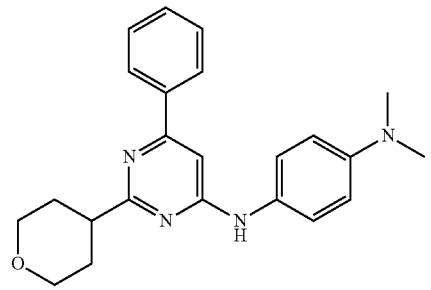 [SMILES: CN(C)c1ccc(Nc2cc(-c3ccccc3)nc(C3CCOCC3)n2)cc1] |

-continued

| Compound number | Structure |
|---|---|
| 17 | 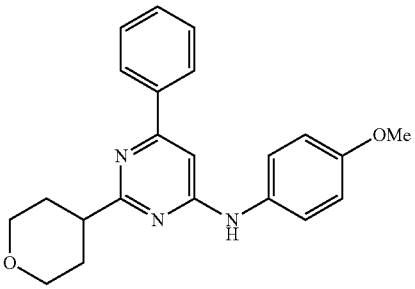 [SMILES: COc1ccc(Nc2cc(-c3ccccc3)nc(C3CCOCC3)n2)cc1] |

The compounds exemplified in this invention may be prepared from readily available starting materials using the following general methods and procedures for example exemplified in Michael Smith, Jerry March—March's Advanced Organic Chemistry: reactions mechanisms and structure—6th Edition, John Wiley & Sons Inc., 2007.

It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—Protective Groups in Organic Synthesis, Fourth Edition, John Wiley & Sons Inc., 2006.

It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures.

The synthesis of a compound of Formula (I), according to the synthetic processes described below, can be conducted in a stepwise manner, whereby each intermediate is isolated and purified by standard purification techniques such as, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds of Formula (I), prepared with the methods described herein below, may be treated or purified by conventional techniques or means for example by filtration, distillation, chromatography, recrystallization and combination thereof.

The salts of compounds of Formula (I) may be prepared by reacting a basic compound with the desired acid in solution.

A second aspect of the present invention is related to a pharmaceutical composition comprising a compound of Formula (I) as disclosed above and a pharmaceutically acceptable carrier, stabilizer, diluent or excipient thereof.

A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, subcutaneous, intravenous, intramuscular, intranasal, topical, intratumoral injection, and pulmonary routes.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

Topical administration of the pharmaceutical compositions is especially useful when the desired treatment involves areas or organs readily accessible by topical application. For application topically to the skin, the pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. Topically-transdermal patches and iontophoretic administration are also described.

Compositions for pulmonary administration include, but are not limited to, dry powder compositions consisting of the powder of a compound of Formula (I) or a salt thereof, and the powder of a suitable carrier and/or lubricant. The compositions for pulmonary administration can be inhaled from any suitable dry powder inhaler device known to a person skilled in the art.

The compounds of this invention can also be administered by intratumoral injection, or injection directly into the tumor vasculature. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. In the case of surgical intervention, the present invention may be used preoperatively, to render an inoperable tumor subject to resection.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I) per dosage unit for daily administration.

In some embodiments, the amounts effective for a specific formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

Concerning formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro Ark. ed. 20th Edition, 2000, Williams & Wilkins Pa., USA, and Remington: The Science and Practice of Pharmacy, 21st Edition, Lippincott Williams & Wilkins Eds., 2005; and in Ansel's Pharmaceutical Dosage Forms and Drug Delivery Systems, 8th Edition, Lippincott Williams & Wilkins Eds., 2005.

The above described components for orally administered or injectable compositions are merely representative.

The compounds of this invention can also be administered in sustained release forms or from sustained release drug delivery systems.

The compounds of formula (I) may be used as a stand-alone therapeutic agent, or in combination with other chemotherapeutics having different mode of actions. The preferred combining chemotherapeutic agents is selected from the group consisting of cisplatin, carboplatin, nedaplatin, oxaliplatin, satraplatin, triplatin tetra nitrate, as well as non-classical alkylating agents like dacarbazine and temozolamide. The compounds of formula (I) may also be used in combination with radiation therapy.

A third aspect of the present invention is related to the use of compounds of Formula (I) as disclosed above or the pharmaceutical composition thereof, or their pharmaceutically acceptable salts or solvates as a medicament.

In particular, compounds of Formula (I) can be used in the treatment of diseases or disorders associated to increased (relative to physiological or desired) RhoJ/Cdc42 levels of expression or function. In particular, the compounds of formula (I) may act as inhibitors of the RhoJ-PAK, more particularly they may be used in the treatment of primary and metastatic neoplastic diseases, pre-malignant conditions, such as hyperplasia, metaplasia or dysplasia, cancer, cancer metastasis, benign tumors, hyperproliferative disorders, cardiomyopathies and retinal disorders. Preferably, the compounds of formula (I) are used in the treatment of melanoma.

In the following, the present invention shall be illustrated by means of some examples, which are not construed to be viewed as limiting the scope of the invention.

The following abbreviations are hereinafter used in the accompanying examples: acetic acid (AcOH), acetonitrile (ACN), ammonia ($NH_3$), deuterated chloroform ($CDCl_3$), deuterated dimethylsulfoxide (DMSO-$d_6$), dichloromethane (DCM), diethyl ether ($Et_2O$), dimethylsulfoxide (DMSO), ethanol (EtOH), ethyl acetate (AcOEt), hydrochloric acid (HCl), tert-butylmethyl ether (TBME), methanol (MeOH), room temperature (rt), sodium bicarbonate ($NaHCO_3$), sodium hydroxide (NaOH), sodium sulphate ($Na_2SO_4$), dichloro[1,1'-bis(diphenylphosphino)ferrocene] palladium dichloromethane complex ($PdCl_2$(dppf) dichloromethane complex), water ($H_2O$).

Chemicals, Materials and Methods
Synthesis

All the commercial available reagents and solvents were used as purchased from vendors without further purification. Dry solvents were purchased from Sigma-Aldrich. Automated column chromatography purifications were done using a Teledyne ISCO apparatus (CombiFlash® Rf) with pre-packed silica gel columns of different sizes (from 4 g up to 120 g) and mixtures of increasing polarity of cyclohexane and ethyl acetate (AcOEt), cyclohexane and tert-butylMethyl eter (TBME) or dicloromethane (DCM) and methanol (MeOH).

Characterizations

NMR experiments were run on a Bruker Avance III 400 system (400.13 MHz for $^1$H), equipped with a BBI probe and Z-gradients. Spectra were acquired at 300 K, using deuterated dimethylsulfoxide (DMSO-$d_6$) or deuterated chloroform ($CDCl_3$) as solvents. For $^1$H-NMR, data are reported as follows: chemical shift, multiplicity (s=singlet, d=doublet, dd=double of doublets, t=triplet, q=quartet, m=multiplet), coupling constants (Hz) and integration. UPLC/MS analyses were run on a Waters ACQUITY UPLC/MS system consisting of a SQD (single quadrupole detector) mass spectrometer equipped with an electrospray ionization interface and a photodiode array detector. The PDA range was 210-400 nm. Analyses were performed on an ACQUITY UPLC BEH C18 column (100×2.1 mmID, particle size 1.7 μm) with a VanGuard BEH C18 pre-column (5×2.1 mmID, particle size 1.7 μm). Mobile phase was 10 mM $NH_4OAc$ in $H_2O$ at pH 5 adjusted with $CH_3COOH$ (A) and 10 mM $NH_4OAc$ in $CH_3CN$—$H_2O$ (95:5) at pH 5.0. For analysis method 1, mobile-phase B proportion increased from 5% to 95% in 3 minutes. For analysis method 2, mobile-phase B proportion increased from 50% to 100% in 3 min. Electrospray ionization in positive and negative mode was applied. ESI was applied in positive and negative mode. All tested compounds showed ≥90% purity by NMR and UPLC/MS analysis.

PREPARATIONS AND EXAMPLES

General scheme

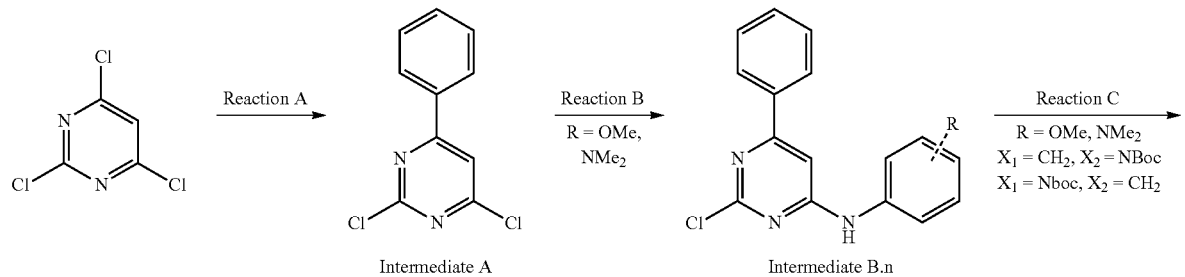

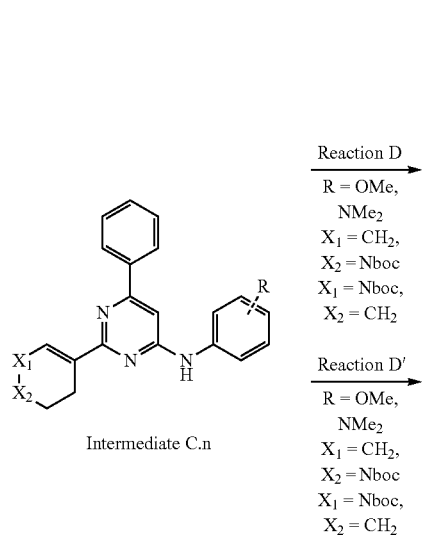

Intermediate C.n

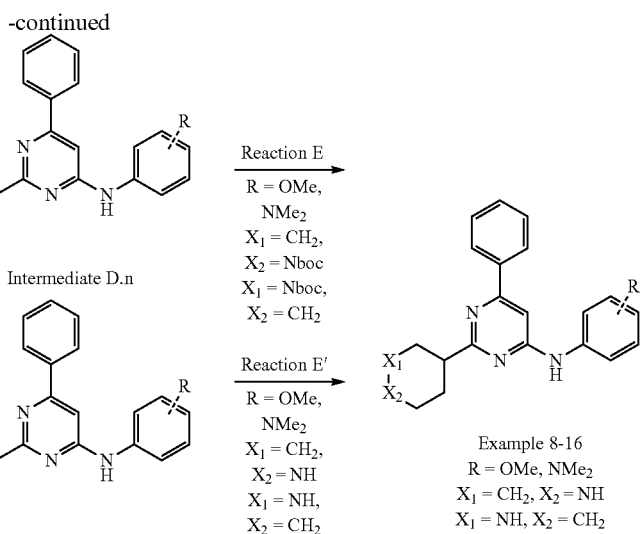

Intermediate D.n

Intermediate D'.n

Example 8-16
R = OMe, NMe₂
X₁ = CH₂, X₂ = NH
X₁ = NH, X₂ = CH₂

Reaction A. Phenylboronic acid (1 eq), K₂CO₃ 2M (2 eq), PdCl₂(dppf).DCM (0.05 eq), 1,4-dioxane, 60° C., microwave, Ar, 1 h, Yield=72%. Reaction B. Aniline derivative (1 eq), Pd(OAc)₂ (0.05 eq), racBINAP (0.05 eq), Cs₂CO₃ (1.2 eq), 1,4-diaxane, Ar, 60° C., microwave, 4 h. Reaction C. 4,4,5,5-tetramethylboronate (1.2 eq), K₂CO₃, 2M (2 eq), PdCl₂(dppf).DCM (0.05 eq), 1,4-dioxane, 120° C., microwave, Ar, 2 h. Reactions D and E'. HCOONH₄ (4 eq), Pd(OH)₂/C (20% weight), MeOH, reflux, N₂, 4 h, or H-cube apparatus (Pd(OH)₂ cartridge, 50° C., 50 bar). Reaction D' and E. HCl (4M), 1,4-dioxane, 0° C. to rt, 1 h.

Scheme 1

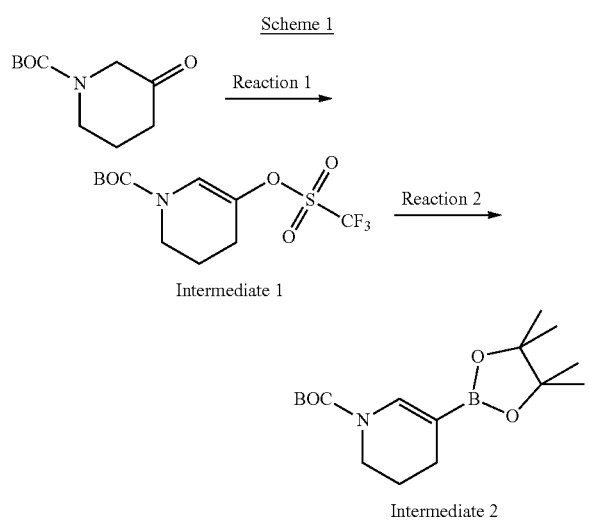

Intermediate 1

Intermediate 2

Reaction 1. 1,1,1-trifluoro-N-phenyl-N-(trifluoro methylsulfonyl)methanesulfonamide (1.1 eq), LDA 2M THF/heptane/ethylbenzene (1.2 eq), THF (dry), −78° C. to rt, Ar, 16 h, yield 28%. Reaction 2. Bispinacolatodiboron (1.3 eq), KOAc (2.8 eq), PdCl₂ (dppf).DCM (0.1 eq), 1,4-dioxane, 80° C., Ar, 3 h, yield 800.

General Procedure Reaction B. Palladium Catalyzed Aniline Derivatives Coupling.

A mixture of Pd(OAc)₂ (0.05 mmol) and racBINAP (0.05 mmol) in 1,4-dioxane (3 ml) was stirred under Ar flushing for 10 minutes. Then were stepwise added a solution of intermediate A (1 mmol) in 1,4-dioxane (1 ml), a solution of corresponding substituted aniline (1 mmol) in 1,4-dioxane (1 ml) and Cs₂CO₃ (1.2 mmol). The reaction mixture was stirred in a CEM® microwave apparatus at 60° C. for 4 hours, filtrated through a celite coarse patch, rinsed with DCM and concentrated to dryness at low pressure. Final normal phase purification yielded Intermediate B.n.

General Procedure Reaction C. Suzuki Coupling Reaction.

A suspension of compound obtained from general procedure B (1 mmol), corresponding 4,4,5,5-tetramethylboronate (1.2 mmol), PdCl₂(dppf) dichloromethane complex (0.1 mmol) and K₂CO₃ 2M solution (2 mmol) in 1,4-dioxane (10 ml) was stirred in a CEM® microwave apparatus at 120° C. for 2 hours. Resulting crude was portioned between dichloromethane (25 ml), NaHCO₃ saturated solution (25 ml), the organic layer dried over Na₂SO₄ and concentrated to dryness at low pressure. Final normal phase purification yielded Intermediate C.n.

General Procedure Reaction D and E'. Double Bound Reduction.

Method 1. Under N₂ atmosphere, a suspension of compound to be reduced (1 mmol), ammonium formate (4 mmol), Pd(OH)₂/C (20% of starting material weight) was stirred at reflux temperature until reaction completion. Catalyst was filtered off through a celite coarse patch and resulting filtrate concentrated to dryness at low pressure. Final normal phase purification yielded Intermediate D.n.

Method 2. A starting material 0.01 M solution in MeOH or THF was eluted in a H-cube apparatus through a Pd (OH)₂—C cartridge at 50° C. under 50 bar H₂ pressure until reaction completion. Final normal phase purification yielded Intermediate D'.n.

General Procedure Reaction D' and E. Boc Elimination.

To a 0° C. solution of Boc protected compound (1 mmol) in 1,4-dioxane (2.6 ml) was dropwise added a HCl (4M) solution in 1,4-dioxane (2.6 ml, 10 mmol) and the reaction mixture stirred at room temperature for 1 h, then the reaction crude was concentrated to dryness at low pressure, the resulting crude portioned between DCM (20 ml) and NaOH 0.1 M (20 ml), the organic layer dried over Na₂SO₄ and concentrated to dryness at low pressure. Final normal phase purification yielded the compounds of the invention.

Example 1. N1,N1-dimethyl-N4-[6-phenyl-2-(3-piperidyl)pyrimidin-4-yl]benzene-1,4-diamine (compound 8)

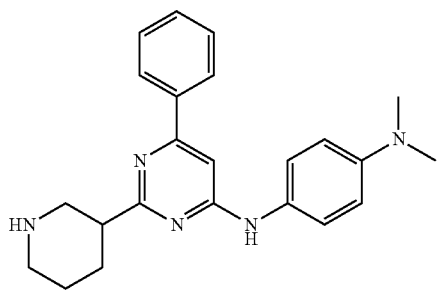 [SMILES: CN(C)c1ccc(Nc2cc(-c3ccccc3)nc(C3CCCNC3)n2)cc1]

Step 1. Synthesis of 2,4-dichloro-6-phenyl-pyrimidine (Intermediate A)

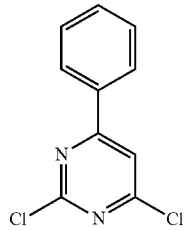 [SMILES: Clc1cc(-c2ccccc2)nc(Cl)n1]

A suspension of 2,4,6-trichloropyrimidine (1000 mg, 5.29 mmol), phenyl boronic acid (665 mg, 5.29 mmol), PdCl$_2$ (dppf) dichloromethane complex (204 mg, 0.26 mmol) and K$_2$CO$_3$ 2 M solution (5.3 ml, 10.58 mmol) in 1,4-dioxane (26.4 ml) was stirred in a CEM® microwave apparatus at 60° C. for 1 hour. Resulting crude was portioned between dichloromethane (150 ml), NaHCO$_3$ saturated solution (100 ml), the organic layer dried over Na$_2$SO$_4$ and concentrated to dryness at low pressure. Final normal phase purification (cyclohexane/DCM from 100/0 to 85/15) afforded pure title compound (857 mg, yield 72%). Rt=1.38 min (analysis method 2); MS (ESI) m/z: 225.1 [M-H]$^+$, [M-H]$^+$ calculated: 225.0. $^1$H NMR (400 MHz, CDCl$_3$) δ 8.13-8.03 (m, 2H), 7.68 (s, 1H), 7.62-7.48 (m, 3H).

Step 2. Synthesis of N1-(2-chloro-6-phenyl-pyrimidin-4-yl)-N4,N4-dimethyl-benzene-1,4-diamine (Intermediate B.1)

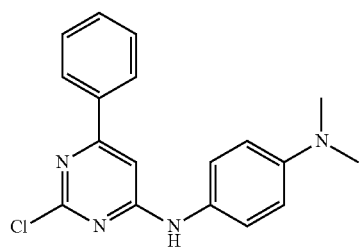 [SMILES: CN(C)c1ccc(Nc2cc(-c3ccccc3)nc(Cl)n2)cc1]

Titled compound was obtained using intermediate A (300 mg, 1.33 mmol) and N1,N1-dimethylbenzene-1,4-diamine (191.1 mg, 1.33 mmol) following the general procedure reaction B previously described. Final normal phase purification (cyclohexane/TBME from 100/0 to 80/20) afforded pure title compound (272 mg, yield 63%). Rt=1.56 min (analysis method 2); MS (ESI) m/z: 325.1 [M-H]$^+$, [M-H]$^+$ calculated: 325.1. $^1$H NMR (400 MHz, DMSO-d$_6$) δ 9.76 (s, 1H), 7.93 (dd, J=6.7, 3.0 Hz, 2H), 7.52 (dd, J=4.6, 2.4 Hz, 3H), 7.36 (s, 2H), 7.00 (s, 1H), 6.87-6.64 (m, 2H), 2.89 (s, 6H).

Step 3. Synthesis of tert-butyl 5-(trifluoro methyl-sulfonyloxy)-3,4-dihydro-2H-pyridine-1-carboxylate (Intermediate 1)

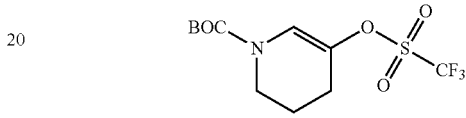

At –78° C., to a solution of lithium diisopropylamide 2.0 M in cyclohexane (8.8 ml, 17.53 mmol) in dry tetrahydrofurane (15.6 ml) was added drop wise a solution of 3-oxo-piperidine-1-carboxyilic acid tert-butyl ester (3000 mg, 14.60 mmol) in dry tetrahydrofurane (15.6 mL). The mixture was stirred at –78° C. for 1 h and a solution of N-phenyl bis trifluoromethanesulfonamide (5855.6 mg, 16.07 mmol) in dry tetrahydrofurane (15.8 mL) was added. The mixture was stirred at –78° C. for 2 h and then was allowed to warm up to room temperature and stirred 16 additional hours at room temperature. The mixture was evaporated to dryness and the residue was taken with diethyl ether (50 ml), washed with water (50 mL), a 2 M solution of sodium hydroxide (50 mL) and brine (50 mL), dried over sodium sulfate and concentrated to dryness at low pressure. Final normal phase purification (cHexane/DCM from 100/0 to 50/50) afforded pure title compound (1354 mg, 28% yield). Rt=2.66 min (analysis method 1). $^1$H NMR (400 MHz, CDCl$_3$) δ 7.07 (s, 1H), 3.52 (s, 2H), 2.43 (td, J=6.4, 1.5 Hz, 2H), 1.93 (tt, J=6.3, 5.0 Hz, 2H), 1.49 (s, 9H).

Step 4. Synthesis of tert-butyl 5-(4,4,5,5-tetramethyl-1,3,2-dioxaborolan-2-yl)-3,4-dihydro-2H-pyridine-1-carboxylate (Intermediate 2)

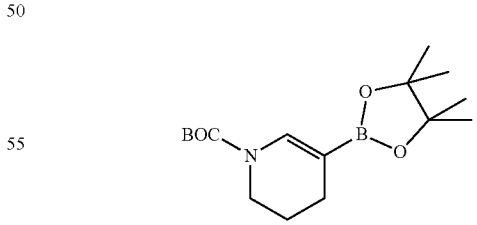

To a degassed solution of intermediate 1 (600 mg, 1.81 mmol) in dioxane (10.7 ml) was added bis-(pinacolato)diboron (603.8 mg, 2.35 mmol), potassium acetate (502.7 mg, 5.07 mmol) and dichloro[1,1'-bis(diphenylphosphino)ferrocene] palladium dichloro methane complex (139.5 mg, 0.18 mmol) were added. The mixture was stirred at 80° C. for 3 h. After cooling down, the mixture was filtered and resulting filtrate concentrated to dryness at low pressure.

Final normal phase purification (cHexane/DCM from 70/30 to 50/50) afforded pure title compound (448 mg, 80% yield). Rt=1.85 min (analysis method 2). MS (ESI) m/z 310.2 [M-H]+, [M-H]+ calculated: 310.2. ¹H NMR (400 MHz, CDCl₃) δ 5.29 (s, 1H), 3.67-3.39 (m, 2H), 2.15-1.96 (m, 2H), 1.81-1.73 (m, 2H), 1.49 (s, 9H), 1.32-1.17 (m, 12H).

Step 5. Synthesis of tert-butyl 5-[4-[4-(dimethylamino)anilino]-6-phenyl-pyrimidin-2-yl]-3,4-dihydro-2H-pyridine-1-carboxylate (Intermediate C.1)

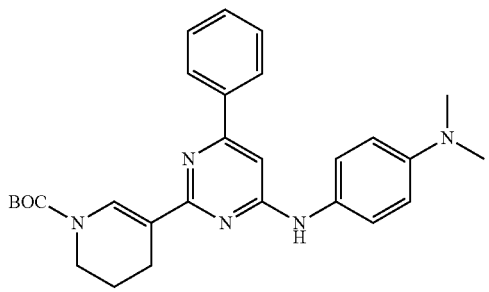 [SMILES: CN(C)c1ccc(Nc2cc(-c3ccccc3)nc(C3=CN(C(=O)OC(C)(C)C)CCC3)n2)cc1]

Titled compound was obtained using intermediate B.1 (100 mg, 0.35 mmol) and intermediate 2 (117.8 mg, 0.37 mmol) following the general procedure reaction C previously described. Final normal phase purification (cyclohexane/AcOEt from 100/0 to 85/15) afforded pure title compound (107.4 mg, yield 74%). Rt=2.58 min (analysis method 2); MS (ESI) m/z 472.4 [M-H]+, [M-H]+ calculated: 472.3. ¹H NMR (400 MHz, DMSO-d₆) δ 9.28 (s, 1H), 8.12-7.96 (m, 2H), 7.64-7.42 (m, 5H), 7.15 (s, 1H), 6.96 (s, 1H), 6.86-6.69 (m, 2H), 4.11 (d, J=4.0 Hz, 2H), 3.55 (t, J=5.7 Hz, 2H), 2.87 (s, 6H), 2.67 (d, J=7.0 Hz, 2H), 1.44 (s, 9H).

Step 6. Synthesis of tert-butyl 3-[4-[4-(dimethylamino)anilino]-6-phenyl-pyrimidin-2-yl]piperidine-1-carboxylate (Intermediate D.1)

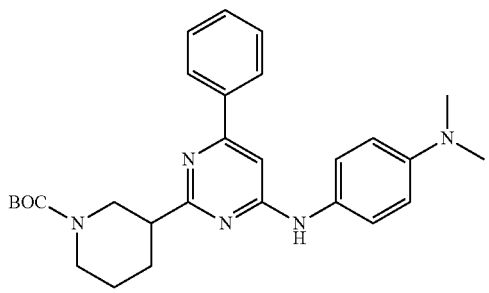 [SMILES: CN(C)c1ccc(Nc2cc(-c3ccccc3)nc(C3CCCN(C(=O)OC(C)(C)C)C3)n2)cc1]

Titled compound was obtained using intermediate C.1 (60.5 mg, 0.12 mmol) following the general procedure D method 2 previously described. Final normal phase purification (cHexane/TBME from 90/10 to 70:30) afforded pure title compound (60 mg, yield 99%). Rt=2.22 min (analysis method 2); MS (ESI) m/z: 474.4 [M-H]+, [M-H]+ calculated: 474.3. ¹H NMR (400 MHz, DMSO-d₆) δ 9.38 (s, 1H), 8.24-7.80 (m, 2H), 7.59-7.34 (m, 5H), 6.98 (s, 1H), 6.91-6.59 (m, 2H), 3.37 (d, J=9.8 Hz, 1H), 3.16-3.02 (m, 1H), 3.02-2.91 (m, 2H), 2.87 (s, 6H), 2.68 (td, J=11.9, 3.0 Hz, 1H), 2.23-2.05 (m, 1H), 1.89-1.70 (m, 2H), 1.63 (q, J=12.8 Hz, 1H), 1.45 (s, 9H).

Step 7. Synthesis of N1,N1-dimethyl-N4-[6-phenyl-2-(3-piperidyl)pyrimidin-4-yl]benzene-1,4-diamine (Compound 8)

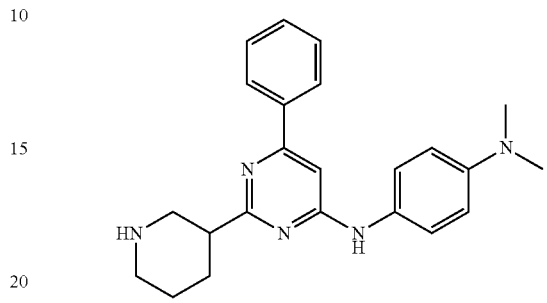

Titled compound was obtained using intermediate D.1 (61 mg, 0.13 mmol) following the general procedure reaction E previously described. Final normal phase purification (DCM/DCM:NH₃ 1M MeOH 4:1 from 80/20 to 60/40) afforded pure title compound (46 mg, yield 95%). Rt=1.96 min (analysis method 1); MS (ESI) m/z: 374.6 [M-H]+, [M-H]+ calculated: 374.2. ¹H NMR (400 MHz, DMSO-d₆) δ 9.38 (s, 1H), 8.24-7.80 (m, 2H), 7.59-7.34 (m, 5H), 6.98 (s, 1H), 6.91-6.59 (m, 2H), 3.37 (d, J=9.8 Hz, 1H), 3.16-3.02 (m, 1H), 3.02-2.91 (m, 2H), 2.87 (s, 6H), 2.68 (td, J=11.9, 3.0 Hz, 1H), 2.23-2.05 (m, 1H), 1.89-1.70 (m, 2H), 1.63 (q, J=12.8 Hz, 1H).

Example 2. N-(4-methoxyphenyl)-6-phenyl-2-(3-piperidyl) pyrimidin-4-amine (Compound 9)

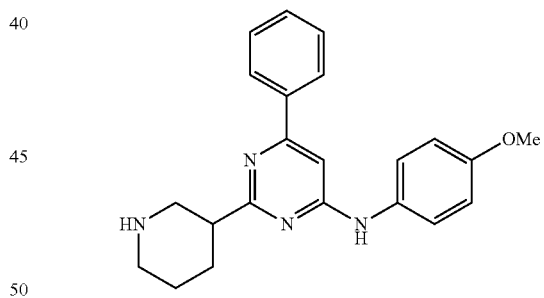

Step 1. Synthesis of 2-chloro-N-(4-methoxyphenyl)-6-phenyl-pyrimidin-4-amine (Intermediate B.2)

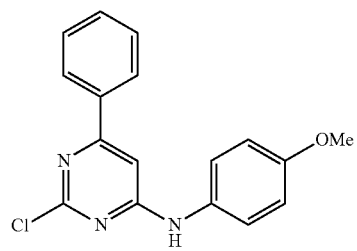 [SMILES: COc1ccc(Nc2cc(-c3ccccc3)nc(Cl)n2)cc1]

Titled compound was obtained using intermediate A (100 mg, 0.44 mmol) and p-methoxyaniline (55.2 mg, 0.44 mmol) following the general procedure reaction B previously described. Final normal phase purification (cyclohexane/TBME from 95/5 to 75/25) afforded pure title compound (86.8 mg, yield 63%). Rt=1.39 min (analysis method 2); MS (ESI) m/z: 312.1 [M-H]+, [M-H]+ calculated: 312.1. ¹H NMR (400 MHz, DMSO-d₆) δ 9.91 (s, 1H), 8.06-7.84 (m, 2H), 7.65-7.37 (m, 5H), 7.06 (s, 1H), 7.02-6.92 (m, 2H), 3.76 (s, 3H).

Step 2. Synthesis of tert-butyl 5-[4-(4-methoxyanilino)-6-phenyl-pyrimidin-2-yl]-3,4-dihydro-2H-pyridine-1-carboxylate (Intermediate C.2)

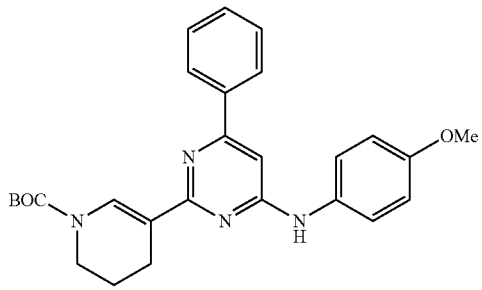 [SMILES: COc1ccc(Nc2cc(-c3ccccc3)nc(C3=CN(C(=O)OC(C)(C)C)CCC3)n2)cc1]

Titled compound was obtained using intermediate B.2 (100 mg, 0.32 mmol) and intermediate 2 (119.0 mg, 0.38 mmol) following the general procedure C previously described. Final normal phase purification (cyclohexane/AcOEt from 100/0 to 80/20) afforded pure title compound (64.7 mg, yield 44%). Rt=2.37 min (analysis method 2); MS (ESI) m/z 459.6 [M-H]+, [M-H]+ calculated: 459.2. ¹H NMR (400 MHz, CDCl₃) δ 8.05-7.97 (m, 2H), 7.46-7.37 (m, 3H), 7.31 (t, J=6.5 Hz, 2H), 6.98-6.90 (m, 2H), 6.71 (s, 1H), 6.68-6.46 (m, 1H), 3.84 (s, 3H), 3.66 (d, J=9.5 Hz, 2H), 2.82-2.60 (m, 2H), 2.02-1.86 (m, 2H), 1.56 (s, 9H).

Step 3. Synthesis of tert-butyl 3-[4-(4-methoxyanilino)-6-phenyl-pyrimidin-2-yl]piperidine-1-carboxylate (Intermediate D.2)

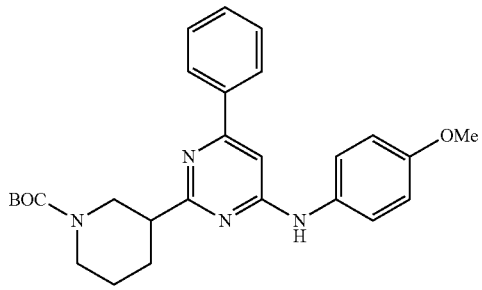 [SMILES: COc1ccc(Nc2cc(-c3ccccc3)nc(C3CCCN(C(=O)OC(C)(C)C)C3)n2)cc1]

Titled compound was obtained using intermediate C.2 (65.0 mg, 0.14 mmol) following the general procedure reaction D method 2 previously described. Final normal phase purification (cHexane/TBME from 100/0 to 80/20) afforded pure title compound (40 mg, yield 62%). Rt=1.94 min (analysis method 2); MS (ESI) m/z: 461.2 [M-H]+, [M-H]+ calculated: 461.2. ¹H NMR (400 MHz, CDCl₃) δ 8.07-7.80 (m, 2H), 7.46-7.38 (m, 3H), 7.26 (s, 1H), 7.01-6.89 (m, 2H), 6.77 (s, 1H), 6.71 (s, 1H), 3.84 (s, 3H), 3.01-2.68 (m, 2H), 2.23 (d, J=12.3 Hz, 1H), 1.80 (qd, J=13.0, 3.8 Hz, 2H), 1.73-1.52 (m, 4H), 1.47 (s, 9H).

Step 4. Synthesis of N-(4-methoxyphenyl)-6-phenyl-2-(3-piperidyl)pyrimidin-4-amine (Compound 9)

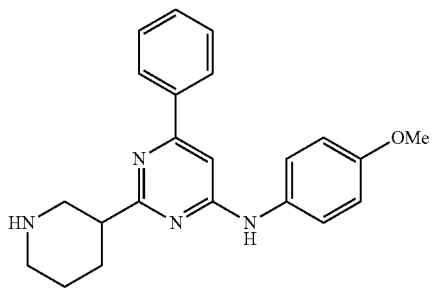 [SMILES: COc1ccc(Nc2cc(-c3ccccc3)nc(C3CCCNC3)n2)cc1]

Titled compound was obtained using intermediate D.2 (40 mg, 0.09 mmol) following the general procedure reaction E previously described. Final normal phase purification (DCM/DCM:NH₃ 1M MeOH 4:1 from 85/15 to 65/35) afforded pure title compound (31 mg, yield 99%). Rt=0.49 min (analysis method 2); MS (ESI) m/z: 361.6 [M-H]+, [M-H]+ calculated: 361.2. ¹H NMR (400 MHz, DMSO-d₆) δ 9.60 (s, 1H), 8.15-7.90 (m, 2H), 7.59 (d, J=8.4 Hz, 2H), 7.56-7.47 (m, 3H), 7.05 (d, J=4.2 Hz, 1H), 7.00-6.90 (m, 2H), 3.76 (s, 3H), 3.60 (d, J=11.9 Hz, 1H), 3.33-3.11 (m, 3H), 2.96-2.91 (m, 1H), 2.26-2.19 (m, 1H), 1.97-1.65 (m, 2H).

Example 3. N3,N3-dimethyl-N1-[6-phenyl-2-(3-piperidyl) pyrimidin-4-yl]benzene-1,3-diamine (Compound 10)

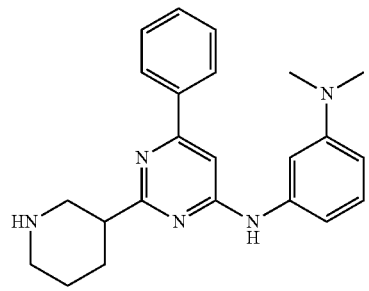 [SMILES: CN(C)c1cccc(Nc2cc(-c3ccccc3)nc(C3CCCNC3)n2)c1]

Step 1. Synthesis of N1-(2-chloro-6-phenyl-pyrimidin-4-yl)-N3,N3-dimethyl-benzene-1,3-diamine (Intermediate B.3)

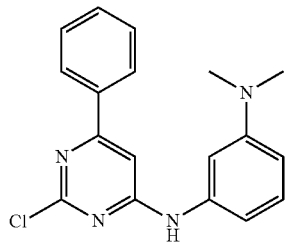 [SMILES: CN(C)c1cccc(Nc2cc(-c3ccccc3)nc(Cl)n2)c1]

Titled compound was obtained using intermediate A (300 mg, 1.13 mmol) and N1,N1-dimethylbenzene-1,3-diamine (181.5 mg, 1.33 mmol) following the general procedure reaction B previously described. Final normal phase purification (cyclohexane/TBME from 100/0 to 80/20) afforded pure title compound (246 mg, yield 57%). Rt=1.73 min (analysis method 2); MS (ESI) m/z: 325.1 [M-H]$^+$, [M-H]$^+$ calculated: 325.1. $^1$H NMR (400 MHz, DMSO-d$_6$) δ 9.93 (s, 1H), 8.14-7.82 (m, 2H), 7.60-7.47 (m, 3H), 7.29-7.09 (m, 2H), 7.04 (s, 1H), 6.99-6.85 (m, 1H), 6.51 (ddd, J=8.4, 2.5, 0.8 Hz, 1H), 2.92 (s, 6H).

Step 2. Synthesis of tert-butyl 5-[4-[3-(dimethylamino)anilino]-6-phenyl-pyrimidin-2-yl]-3,4-dihydro-2H-pyridine-1-carboxylate (Intermediate C.3)

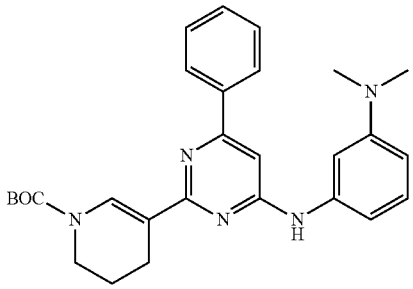 [SMILES: CN(C)c1cccc(Nc2cc(-c3ccccc3)nc(C3=CN(C(=O)OC(C)(C)C)CCC3)n2)c1]

Titled compound was obtained using intermediate B.3 (175 mg, 0.54 mmol) and intermediate 2 (199.9 mg, 0.65 mmol) following the general procedure reaction C previously described. Final normal phase purification (cyclohexane/AcOEt from 100/0 to 85/15) afforded pure title compound (109.2 mg, yield 43%). Rt=2.65 min (analysis method 2); MS (ESI) m/z 472.3 [M-H]$^+$, [M-H]$^+$ calculated: 472.3. $^1$H NMR (400 MHz, DMSO-d$_6$) δ 9.34 (s, 1H), 8.40 (s, 1H), 8.04 (dd, J=7.7, 1.9 Hz, 2H), 7.59-7.44 (m, 4H), 7.11 (t, J=8.0 Hz, 2H), 6.99 (s, 1H), 6.40 (dd, J=9.1, 2.5 Hz, 1H), 3.59 (t, J=5.6 Hz, 2H), 2.92 (s, 6H), 2.65-2.59 (m, 2H), 1.88 (p, J=6.0 Hz, 2H), 1.50 (s, 9H).

Step 3. Synthesis of tert-butyl 3-[4-[3-(dimethylamino)anilino]-6-phenyl-pyrimidin-2-yl]piperidine-1-carboxylate (Intermediate D.3)

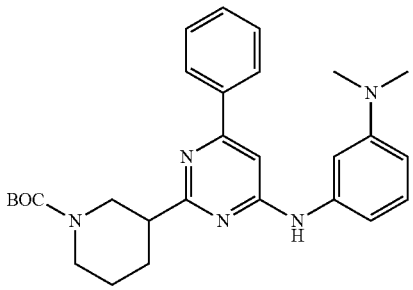 [SMILES: CN(C)c1cccc(Nc2cc(-c3ccccc3)nc(C3CCCN(C(=O)OC(C)(C)C)C3)n2)c1]

Titled compound was obtained using intermediate C.3 (105 mg, 0.22 mmol) following the general procedure reaction D method previously described. Final normal phase purification (cHexane/AcOEt from 100/0 to 80/20) afforded pure title compound (12 mg, yield 12%). Rt=2.35 min (analysis method 2); MS (ESI) m/z: 474.6 [M-H]$^+$, [M-H]$^+$ calculated: 474.3. $^1$H NMR (400 MHz, CDCl$_3$) δ 8.04-7.93 (m, 2H), 7.49-7.37 (m, 4H), 7.04 (s, 1H), 6.78 (s, 1H), 6.69 (d, J=7.7 Hz, 1H), 6.59 (d, J=8.5 Hz, 1H), 4.20-4.08 (m, 1H), 3.23-3.16 (m, 1H), 2.99 (s, 6H), 2.98-2.91 (m, 1H), 2.88-2.77 (m, J=14.3 Hz, 1H), 2.31-2.20 (m, 1H), 1.82-1.58 (m, 2H), 1.51-1.45 (m, 11H).

Step 4. Synthesis of N3,N3-dimethyl-N1-[6-phenyl-2-(3-piperidyl)pyrimidin-4-yl]benzene-1,3-diamine (Compound 10)

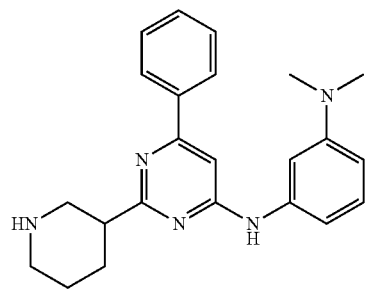 [SMILES: CN(C)c1cccc(Nc2cc(-c3ccccc3)nc(C3CCCNC3)n2)c1]

Titled compound was obtained using intermediate D.3 (34 mg, 0.08 mmol) following the general procedure reaction E. Final normal phase purification (DCM/DCM:NH$_3$ 1M MeOH 4:1 from 95/5 to 45/55) afforded pure title compound (16 mg, yield 61%). Rt=2.07 min (analysis method 1); MS (ESI) m/z: 374.5 [M-H]$^+$, [M-H]$^+$ calculated: 374.2. $^1$H NMR (400 MHz, DMSO-d$_6$) δ 9.50 (s, 1H), 8.01 (dd, J=7.8, 1.8 Hz, 2H), 7.56-7.48 (m, 3H), 7.46 (s, 1H), 7.12 (t, J=8.1 Hz, 1H), 7.10-7.06 (m, 1H), 6.90 (d, J=8.0 Hz, 1H), 6.40 (dd, J=8.2, 2.5 Hz, 1H), 3.28-3.14 (m, 1H), 2.94 (s, 6H), 2.94-2.87 (m, 1H), 2.84-2.75 (m, 2H), 2.46 (dd, J=12.1, 2.9 Hz, 1H), 2.16-2.03 (m, 1H), 1.90-1.72 (m, 1H), 1.71-1.58 (m, 1H), 1.57-1.39 (m, 1H).

Example 4. N-(3-methoxyphenyl)-6-phenyl-2-(3-piperidyl) pyrimidin-4-amine (Compound 11)

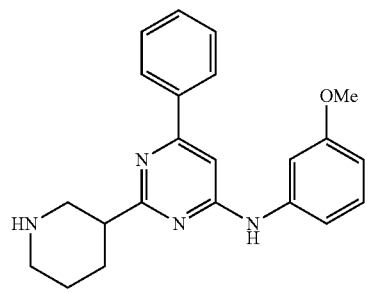 [SMILES: COc1cccc(Nc2cc(-c3ccccc3)nc(C3CCCNC3)n2)c1]

Step 1. Synthesis of 2-chloro-N-(3-methoxyphenyl)-6-phenyl-pyrimidin-4-amine (Intermediate B.4)

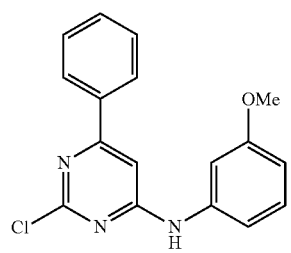 [SMILES: COc1cccc(Nc2cc(-c3ccccc3)nc(Cl)n2)c1]

Titled compound was obtained using intermediate A (300 mg, 1.13 mmol) and m-methoxyaniline (154 μl, 1.33 mmol) following the general procedure reaction B previously described. Final normal phase purification (cyclohexane/TBME from 100/0 to 85/15) afforded pure title compound (150 mg, yield 36%). Rt=1.52 min (analysis method 2); MS (ESI) m/z: 312.1 [M-H]+, [M-H]+ calculated: 312.1. $^1$H NMR (400 MHz, DMSO-d$_6$) δ 10.07 (s, 1H), 8.00-7.90 (m, 2H), 7.59-7.50 (m, 3H), 7.34 (t, J=2.3 Hz, 1H), 7.29 (t, J=8.1 Hz, 1H), 7.18 (s, 2H), 6.69 (ddd, J=8.2, 2.5, 0.9 Hz, 1H), 3.77 (s, 3H).

Step 2. Synthesis of tert-butyl 5-[4-(3-methoxyanilino)-6-phenyl-pyrimidin-2-yl]-3,4-dihydro-2H-pyridine-1-carboxylate (Intermediate C.4)

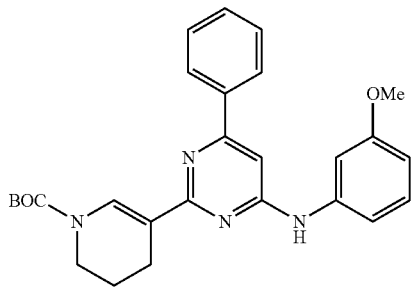 [SMILES: COc1cccc(Nc2cc(-c3ccccc3)nc(C3=CN(C(=O)OC(C)(C)C)CCC3)n2)c1]

Titled compound was obtained using intermediate B.4 (100 mg, 0.32 mmol) and intermediate 2 (119.0 mg, 0.38 mmol) following the general procedure reaction C previously described. Final normal phase purification (cyclohexane/TBME from 100/0 to 80/20) afforded pure title compound (65.0 mg, yield 44%).

Rt=2.40 min (method 2); MS (ESI) m/z 459.6 [M-H]+, [M-H]+ calculated: 459.2.

Step 3. Synthesis of tert-butyl 3-[4-(3-methoxyanilino)-6-phenyl-pyrimidin-2-yl]piperidine-1-carboxylate (Intermediate D.4)

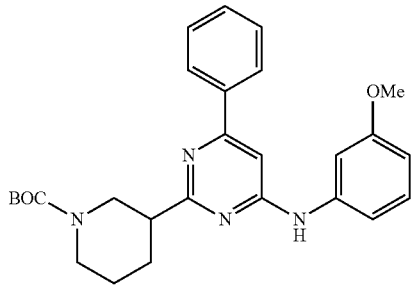 [SMILES: COc1cccc(Nc2cc(-c3ccccc3)nc(C3CCCN(C(=O)OC(C)(C)C)C3)n2)c1]

Titled compound was obtained using intermediate C.4 (65.0 mg, 0.14 mmol) following the general procedure reaction D method 2 previously described. Final normal phase purification (cHexane/AcOEt from 100/0 to 80:20) afforded pure title compound (32.6 mg, yield 50%). Rt=2.13 min (analysis method 2); MS (ESI) m/z: 461.6 [M-H]+, [M-H]+ calculated: 461.2. $^1$H NMR (400 MHz, CDCl$_3$) δ 8.04-7.92 (m, 2H), 7.45 (p, J=3.9, 3.2 Hz, 3H), 7.30 (t, J=8.1 Hz, 1H), 7.08 (t, J=2.2 Hz, 1H), 6.99 (s, 1H), 6.95 (dd, J=7.9, 2.0 Hz, 1H), 6.89 (s, 1H), 6.72 (dd, J=8.3, 2.4 Hz, 1H), 3.84 (s, 3H), 3.20 (s, 1H), 2.99-2.88 (m, 1H), 2.80 (t, J=12.5 Hz, 1H), 2.26 (d, J=12.5 Hz, 1H), 1.93-1.74 (m, 2H), 1.75-1.51 (m, 3H), 1.47 (s, 9H).

Step 4. Synthesis of N-(3-methoxyphenyl)-6-phenyl-2-(3-piperidyl)pyrimidin-4-amine (Compound 11)

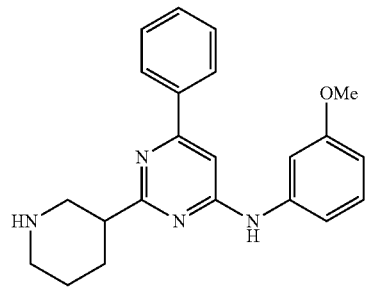 [SMILES: COc1cccc(Nc2cc(-c3ccccc3)nc(C3CCCNC3)n2)c1]

Titled compound was obtained using intermediate D.4 (61 mg, 0.13 mmol) following the general procedure reaction E. Final normal phase purification (DCM/DCM:NH$_3$ 1M MeOH 4:1 from 85/15 to 60/40) afforded pure title compound (39 mg, yield 82%). Rt=1.91 min (analysis method 1); MS (ESI) m/z: 361.6 [M-H]+, [M-H]+ calculated: 361.2. $^1$H NMR (400 MHz, DMSO-d$_6$) δ 9.89 (s, 1H), 8.17-7.94 (m, 2H), 7.67-7.44 (m, 4H), 7.34-7.12 (m, 3H), 6.61 (dt, J=5.4, 2.4 Hz, 1H), 3.79 (s, 3H), 3.63 (d, J=8.1 Hz, 1H), 3.27-3.18 (m, 3H), 2.89 (d, J=14.1 Hz, 1H), 2.26 (d, J=11.7 Hz, 1H), 2.01-1.67 (m, 3H).

Example 5. N4,N4-dimethyl-N1-[6-phenyl-2-(4-piperidyl) pyrimidin-4-yl]benzene-1,4-diamine (Compound 12)

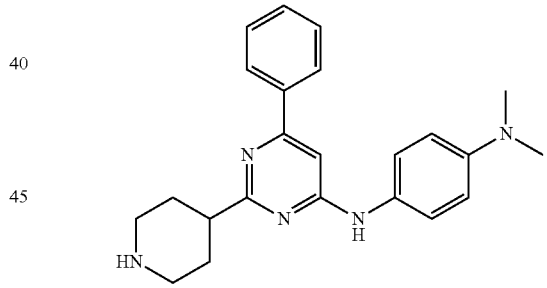

Step 1. Synthesis of tert-butyl 4-[4-[4-(dimethylamino) anilino]-6-phenyl-pyrimidin-2-yl]-3,6-dihydro-2H-pyridine-1-carboxylate (Intermediate C.5)

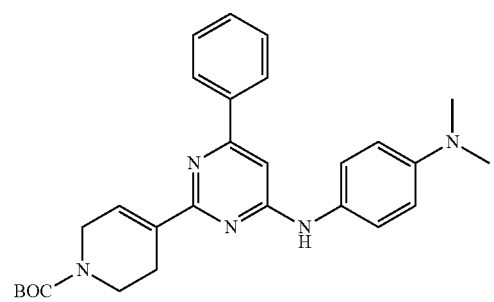 [SMILES: CN(C)c1ccc(Nc2cc(-c3ccccc3)nc(C3=CCN(C(=O)OC(C)(C)C)CC3)n2)cc1]

Titled compound was obtained using intermediate B.1 (100 mg, 0.35 mmol) and tert-butyl 4-(4,4,5,5-tetramethyl-1,3,2-dioxaborolan-2-yl)-3,6-dihydro-2H-pyridine-1-carboxylate (117.8 mg, 0.37 mmol) following the general procedure reaction C previously described. Final normal phase purification (cyclohexane/AcOEt from 100/0 to 85/15) afforded pure title compound (107.4 mg, yield 74%). Rt=2.58 min (analysis method 2); MS (ESI) m/z 472.4 [M-H]$^+$, [M-H]$^+$ calculated: 472.3. $^1$H NMR (400 MHz, DMSO-d$_6$) δ 9.28 (s, 1H), 8.12-7.96 (m, 2H), 7.64-7.42 (m, 5H), 7.15 (s, 1H), 6.96 (s, 1H), 6.86-6.69 (m, 2H), 4.11 (d, J=4.0 Hz, 2H), 3.55 (t, J=5.7 Hz, 2H), 2.87 (s, 6H), 2.67 (d, J=7.0 Hz, 2H), 1.44 (s, 9H).

Step 2. Synthesis of N4,N4-dimethyl-N1-[6-phenyl-2-(1,2,3,6-tetrahydropyridin-4-yl)pyrimidin-4-yl]benzene-1,4-diamine (Intermediate D'.5)

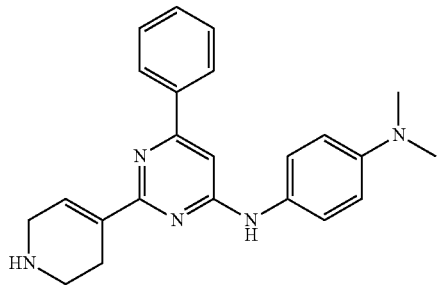 [SMILES: CN(C)c1ccc(Nc2cc(-c3ccccc3)nc(C3=CCNCC3)n2)cc1]

Titled compound was obtained using intermediate C.5 (106 mg, 0.22 mmol) following the general procedure reaction D' (84 mg, yield 99%). Rt=0.72 min (analysis method 2); MS (ESI) m/z: 372.5 [M-H]$^+$, [M-H]$^+$ calculated: 372.2. Resulting solid was used in next step without any further purification procedure.

Step 3. Synthesis of N4,N4-dimethyl-N1-[6-phenyl-2-(4-piperidyl)pyrimidin-4-yl]benzene-1,4-diamine (Compound 12)

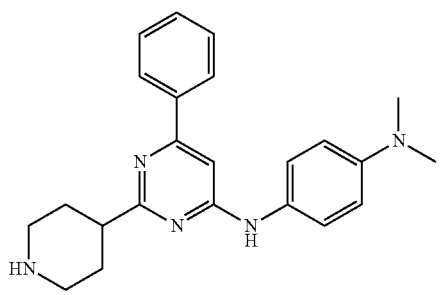 [SMILES: CN(C)c1ccc(Nc2cc(-c3ccccc3)nc(C3CCNCC3)n2)cc1]

Titled compound was obtained using intermediate D'0.5 (84 mg, 0.22 mmol) following the general procedure reaction E' method previously described. Final normal phase purification (DCM/DCM:NH$_3$ 1M MeOH 4:1 from 70/30 to 50/50) afforded pure title compound (54 mg, yield 64%). Rt=1.98 min (analysis method 1); MS (ESI) m/z: 374.2 [M-H]$^+$, [M-H]$^+$ calculated: 374.2. $^1$H NMR (400 MHz, DMSO-d$_6$). δ 9.25 (s, 1H), 8.17-7.82 (m, 2H), 7.69-7.37 (m, 5H), 6.93 (s, 1H), 6.83-6.66 (m, 2H), 3.08 (dt, J=12.2, 3.4 Hz, 2H), 2.87 (s, 6H), 2.77 (tt, J=11.5, 3.8 Hz, 1H), 2.66 (td, J=12.1, 2.6 Hz, 2H), 1.93 (dd, J=13.4, 3.5 Hz, 2H), 1.77 (qd, J=13.0, 12.5, 4.0 Hz, 2H).

Example 6. N-(4-methoxyphenyl)-6-phenyl-2-(4-piperidyl)pyrimidin-4-amine (Compound 13)

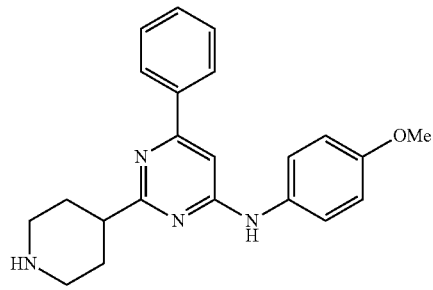 [SMILES: COc1ccc(Nc2cc(-c3ccccc3)nc(C3CCNCC3)n2)cc1]

Step 1. Synthesis of tert-butyl 4-[4-(4-methoxyanilino)-6-phenyl-pyrimidin-2-yl]-3,6-dihydro-2H-pyridine-1-carboxylate (Intermediate C.6)

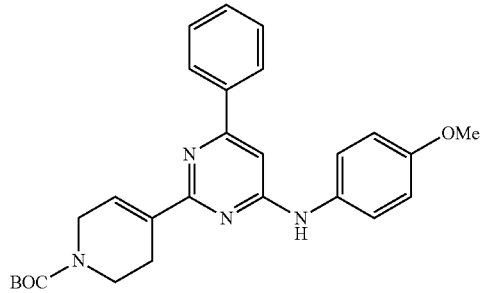 [SMILES: COc1ccc(Nc2cc(-c3ccccc3)nc(C3=CCN(C(=O)OC(C)(C)C)CC3)n2)cc1]

Titled compound was obtained using intermediate B.2 (80 mg, 0.26 mmol) and tert-butyl 4-(4,4,5,5-tetramethyl-1,3,2-dioxaborolan-2-yl)-3,6-dihydro-2H-pyridine-1-carboxylate (98.1 mg, 0.31 mmol) following the general procedure reaction C previously described. Final normal phase purification (cyclohexane/AcOEt from 95/5 to 75/25) afforded pure title compound (104.7 mg, yield 89%). Rt=2.24 min (analysis method 2); MS (ESI) m/z 459.3 [M-H]$^+$, [M-H]$^+$ calculated: 459.2. $^1$H NMR (400 MHz, DMSO-d$_6$) δ 9.44 (s, 1H), 8.12-8.02 (m, 2H), 7.68-7.60 (m, 2H), 7.58-7.46 (m, 3H), 7.17 (s, 1H), 7.01 (s, 1H), 6.99-6.92 (m, 2H), 4.12 (s, 2H), 3.75 (s, 3H), 3.56 (t, J=5.7 Hz, 2H), 2.68 (q, J=4.0, 3.4 Hz, 2H), 1.44 (s, 9H).

Step 2. Synthesis of N-(4-methoxyphenyl)-6-phenyl-2-(1,2,3,6-tetrahydropyridin-4-yl)pyrimidin-4-amine (Intermediate D'.6)

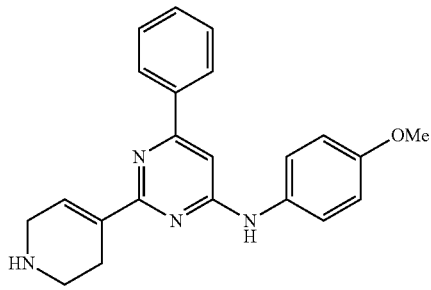 [SMILES: COc1ccc(Nc2cc(-c3ccccc3)nc(C3=CCNCC3)n2)cc1]

Titled compound was obtained using intermediate C.6 (102 mg, 0.22 mmol) following the general procedure reaction D' (80 mg, yield 99%). Rt=0.60 min (analysis method 2); MS (ESI) m/z: 359.2 [M-H]$^+$, [M-H]$^+$ calculated:

359.2. Resulting solid was used in next step without any further purification procedure.

Step 3. Synthesis of N-(4-methoxyphenyl)-6-phenyl-2-(4-piperidyl)pyrimidin-4-amine (Compound 13)

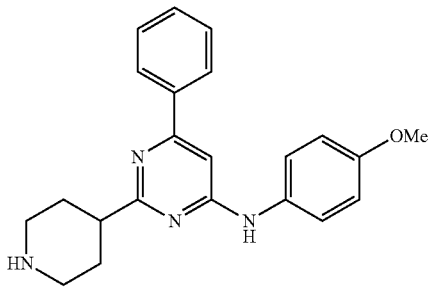 [SMILES: COc1ccc(Nc2cc(-c3ccccc3)nc(C3CCNCC3)n2)cc1]

Titled compound was obtained using intermediate D'0.6 (80 mg, 0.22 mmol) following the general procedure reaction E' method previously described. Final normal phase purification (DCM/DCM:NH₃ 1M MeOH 4:1 from 85/15 to 50/50) afforded pure title compound (52.5 mg, yield 64%). Rt=1.87 min (analysis method 1); MS (ESI) m/z: 361.3 [M-H]⁺, [M-H]⁺ calculated: 361.2. ¹H NMR (400 MHz, DMSO-d₆). δ 9.44 (s, 1H), 8.14-7.89 (m, 2H), 7.64 (d, J=8.9 Hz, 2H), 7.58-7.38 (m, 3H), 6.99 (s, 1H), 6.96-6.91 (m, 2H), 3.75 (s, 3H), 3.13 (d, J=12.4 Hz, 2H), 2.83 (tt, J=11.4, 3.8 Hz, 1H), 2.73 (td, J=12.2, 2.7 Hz, 2H), 1.97 (dd, J=12.8, 3.4 Hz, 2H), 1.81 (qd, J=12.2, 4.0 Hz, 2H).

Example 7. N3,N3-dimethyl-N1-[6-phenyl-2-(4-piperidyl) pyrimidin-4-yl]benzene-1,3-diamine (Compound 14)

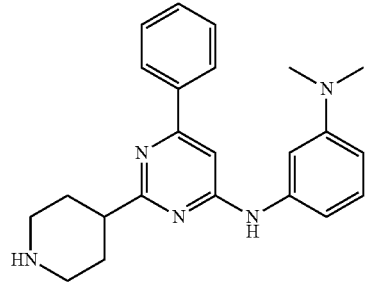 [SMILES: CN(C)c1cccc(Nc2cc(-c3ccccc3)nc(C3CCNCC3)n2)c1]

Step 1. Synthesis of tert-butyl 4-[4-[3-(dimethylamino)anilino]-6-phenyl-pyrimidin-2-yl]-3,6-dihydro-2H-pyridine-1-carboxylate (Intermediate C.7)

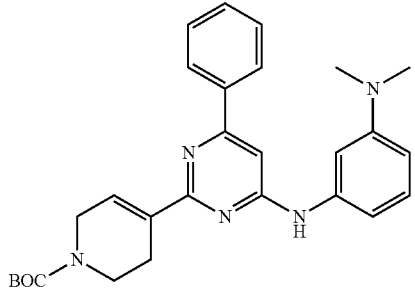 [SMILES: CN(C)c1cccc(Nc2cc(-c3ccccc3)nc(C3=CCN(C(=O)OC(C)(C)C)CC3)n2)c1]

Titled compound was obtained using intermediate B.3 (120 mg, 0.37 mmol) and tert-butyl 4-(4,4,5,5-tetramethyl-1,3,2-dioxaborolan-2-yl)-3,6-dihydro-2H-pyridine-1-carboxylate (129.5 mg, 0.41 mmol) following the general procedure reaction C previously described. Final normal phase purification (cyclohexane/AcOEt from 100/0 to 80/20) afforded title compound (155.1 mg, yield 89%). Rt=2.48 min (analysis method 2); MS (ESI) m/z 472.3 [M-H]⁺, [M-H]⁺ calculated: 472.3. ¹H NMR (400 MHz, DMSO-d₆) δ 9.44 (s, 1H), 8.17-7.95 (m, 2H), 7.67-7.41 (m, 3H), 7.31 (s, 1H), 7.21 (s, 1H), 7.14 (t, J=8.1 Hz, 1H), 7.11 (s, 1H), 7.03-6.93 (m, 1H), 6.42 (ddd, J=8.3, 2.7, 0.8 Hz, 1H), 4.11 (s, 2H), 3.56 (t, J=5.6 Hz, 2H), 2.93 (s, 6H), 2.81-2.62 (m, 2H), 1.44 (s, 9H).

Step 2. Synthesis of tert-butyl 4-[4-[3-(dimethylamino)anilino]-6-phenyl-pyrimidin-2-yl]piperidine-1-carboxylate (Intermediate D.7)

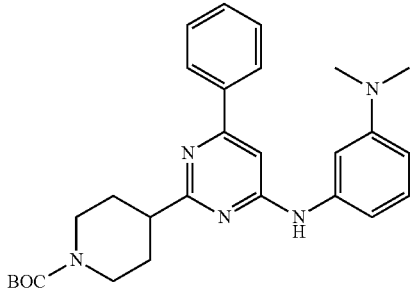 [SMILES: CN(C)c1cccc(Nc2cc(-c3ccccc3)nc(C3CCN(C(=O)OC(C)(C)C)CC3)n2)c1]

Titled compound was obtained using intermediate C.7 (150 mg, 0.32 mmol) following the general procedure reaction D method previously described. Final normal phase purification (cyclohexane/AcOEt from 100/0 to 80/20) afforded pure title compound (149 mg, yield 99%). Rt=2.30 min (analysis method 2); MS (ESI) m/z: 474.4 [M-H]⁺, [M-H]⁺ calculated: 474.3. ¹H NMR (400 MHz, DMSO-d₆) δ 9.43 (s, 1H), 8.08-7.94 (m, 2H), 7.58-7.44 (m, 3H), 7.40 (s, 1H), 7.11 (t, J=8.1 Hz, 1H), 7.06 (s, 1H), 6.88 (ddd, J=7.9, 2.1, 0.8 Hz, 1H), 6.41 (ddd, J=8.4, 2.5, 0.8 Hz, 1H), 4.05 (d, J=13.1 Hz, 2H), 1.98 (dd, J=13.6, 3.5 Hz, 2H), 2.95-2.87 (m, 9H), 1.73 (qd, J=12.5, 4.2 Hz, 2H), 1.42 (s, 9H).

Step 3. Synthesis of N3,N3-dimethyl-N1-[6-phenyl-2-(4-piperidyl)pyrimidin-4-yl]benzene-1,3-diamine (Compound 14)

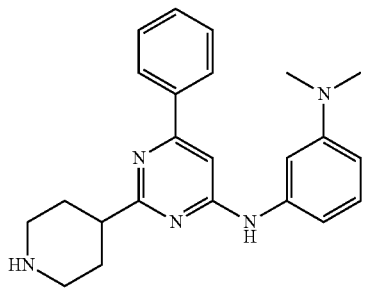

Titled compound was obtained using intermediate D.7 (80 mg, 0.22 mmol) following the general procedure reaction E previously described. Final normal phase purification (DCM/DCM:NH$_3$ 1M MeOH 4:1 from 95/5 to 60/40) afforded pure title compound (39.6 mg, yield 34%). Rt=1.97 min (analysis method 1); MS (ESI) m/z: 374.6 [M-H]$^+$, [M-H]$^+$ calculated: 374.2. $^1$H NMR (400 MHz, DMSO-d$_6$). δ 9.42 (s, 1H), 8.01 (d, J=7.0 Hz, 2H), 7.51 (d, J=7.0 Hz, 3H), 7.40 (s, 1H), 7.12 (t, J=8.1 Hz, 1H), 7.07 (s, 1H), 6.94 (d, J=8.0 Hz, 1H), 6.51-6.33 (m, 1H), 3.03 (d, J=11.9 Hz, 2H), 2.93 (s, 6H), 2.85-2.70 (m, 1H), 2.61 (t, J=11.9 Hz, 2H), 2.00-1.85 (m, 2H), 1.75 (qd, J=12.3, 4.3 Hz, 2H).

Example 8. N-(3-methoxyphenyl)-6-phenyl-2-(4-piperidyl) pyrimidin-4-amine (Compound 15)

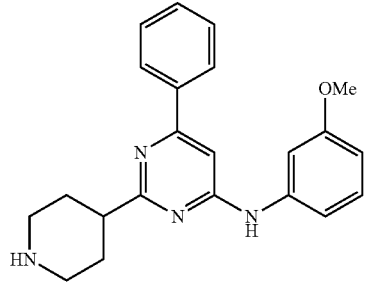 [SMILES: COc1cccc(Nc2cc(-c3ccccc3)nc(C3CCNCC3)n2)c1]

Step 1. Synthesis of tert-butyl 4-[4-(3-methoxyanilino)-6-phenyl-pyrimidin-2-yl]-3,6-dihydro-2H-pyridine-1-carboxylate (Intermediate C.8)

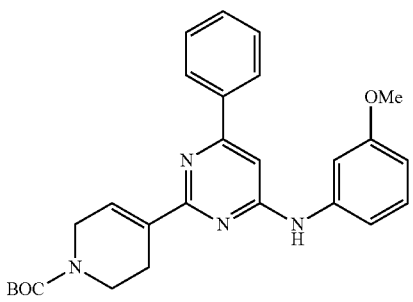 [SMILES: COc1cccc(Nc2cc(-c3ccccc3)nc(C3=CCN(C(=O)OC(C)(C)C)CC3)n2)c1]

Titled compound was obtained using intermediate B.4 (180 mg, 0.58 mmol) and tert-butyl 4-(4,4,5,5-tetramethyl-1,3,2-dioxaborolan-2-yl)-3,6-dihydro-2H-pyridine-1-carboxylate (202.4 mg, 0.64 mmol) following the general procedure reaction C previously described. Final normal phase purification (cyclohexane/AcOEt from 100/0 to 85/15) afforded title compound (241.2 mg, yield 91%). Rt=2.31 min (analysis method 2); MS (ESI) m/z 459.3 [M-H]$^+$, [M-H]$^+$ calculated: 459.2. $^1$H NMR (400 MHz, DMSO-d$_6$) δ 9.63 (s, 1H), 8.19-8.03 (m, 2H), 7.62-7.46 (m, 4H), 7.33-7.22 (m, 2H), 7.20 (s, 1H), 7.11 (s, 1H), 6.67-6.54 (m, 1H), 4.13 (d, J=3.3 Hz, 2H), 3.79 (s, 3H), 3.57 (t, J=5.7 Hz, 2H), 2.71 (s, 2H), 1.44 (s, 9H).

Step 2. Synthesis of tert-butyl 4-[4-(3-methoxyanilino)-6-phenyl-pyrimidin-2-yl]piperidine-1-carboxylate (Intermediate D.8)

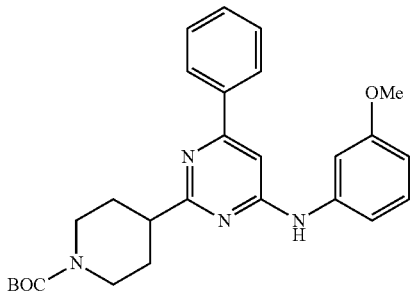 [SMILES: COc1cccc(Nc2cc(-c3ccccc3)nc(C3CCN(C(=O)OC(C)(C)C)CC3)n2)c1]

Titled compound was obtained using intermediate C.8 (240 mg, 0.52 mmol) following the general procedure reaction D method 1 previously described. Final normal phase purification (cyclohexane/AcOEt from 100/0 to 80/20) afforded pure title compound (120 mg, yield 50%). Rt=2.11 min (analysis method 2); MS (ESI) m/z: 461.4 [M-H]$^+$, [M-H]$^+$ calculated: 461.2. $^1$H NMR (400 MHz, DMSO-d$_6$) δ 9.61 (s, 1H), 8.07-7.94 (m, 2H), 7.63 (t, J=2.2 Hz, 1H), 7.57-7.45 (m, 3H), 7.22 (t, J=8.0 Hz, 1H), 7.17 (dt, J=8.3, 1.4 Hz, 1H), 7.08 (s, 1H), 6.59 (ddd, J=8.0, 2.5, 1.1 Hz, 1H), 4.12-3.96 (m, 2H), 3.77 (s, 3H), 2.93 (tt, J=11.4, 3.7 Hz, 3H), 2.06-1.95 (m, 2H), 1.72 (qd, J=12.4, 4.2 Hz, 2H), 1.42 (s, 9H).

Step 3. Synthesis of N-(3-methoxyphenyl)-6-phenyl-2-(4-piperidyl)pyrimidin-4-amine (Compound 15)

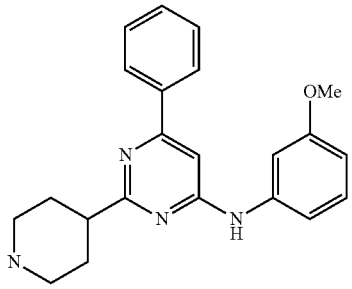 [SMILES: COc1cccc(Nc2cc(-c3ccccc3)nc(C3CCNCC3)n2)c1]

Titled compound was obtained using intermediate D.8 (115 mg, 0.25 mmol) following the general procedure reaction E previously described. Final normal phase purification (DCM/DCM:NH$_3$ 1M MeOH 4:1 from 95/5 to 50/50) afforded pure title compound (80.1 mg, yield 89%). Rt=1.85 min (analysis method 1); MS (ESI) m/z: 361.6 [M-H]$^+$, [M-H]$^+$ calculated: 361.2. $^1$H NMR (400 MHz, DMSO-d6). δ 9.58 (s, 1H), 8.13-7.92 (m, 2H), 7.65 (t, J=2.0 Hz, 1H), 7.59-7.39 (m, 3H), 7.33-7.15 (m, 2H), 7.07 (s, 1H), 6.58 (dt, J=7.2, 2.3 Hz, 1H), 3.78 (s, 3H), 3.04 (dt, J=12.2, 3.3 Hz, 2H), 2.80 (tt, J=11.6, 3.8 Hz, 1H), 2.61 (td, J=12.1, 2.5 Hz, 2H), 2.03-1.85 (m, 2H), 1.74 (qd, J=12.2, 4.0 Hz, 2H).

Example 9. N1,N1-dimethyl-N4-(6-phenyl-2-tetrahydropyran-4-yl-pyrimidin-4-yl)benzene-1,4-diamine (Compound 16)

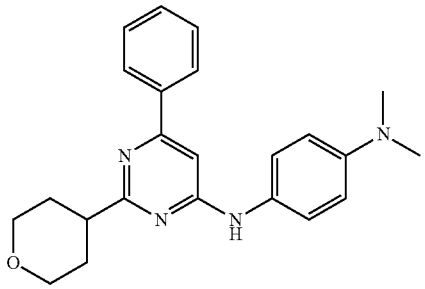 [SMILES: CN(C)c1ccc(Nc2cc(-c3ccccc3)nc(C3CCOCC3)n2)cc1]

Step 1. N1-[2-(3,6-dihydro-2H-pyran-4-yl)-6-phenyl-pyrimidin-4-yl]-N4,N4-dimethyl-benzene-1,4-diamine (Intermediate C.9)

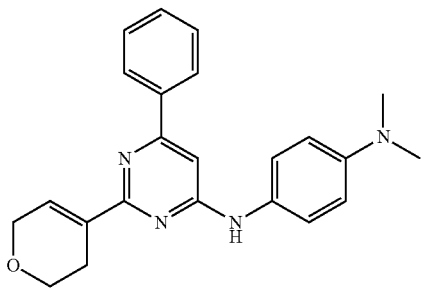 [SMILES: CN(C)c1ccc(Nc2cc(-c3ccccc3)nc(C3=CCOCC3)n2)cc1]

Titled compound was obtained using intermediate B.1 (115 mg, 0.35 mmol) and 3,6-Dihydro-2H-pyran-4-boronic acid pinacol ester (91.1 mg, 0.42 mmol) following the general procedure reaction C previously described. Final normal phase purification (cyclohexane/AcOEt from 90/10 to 70/30) afforded title compound (37.1 mg, yield 28%). Rt=1.70 min (analysis method 2); MS (ESI) m/z 373.5 [M-H]$^+$, [M-H]$^+$ calculated: 373.2. $^1$H NMR (400 MHz, DMSO-d$_6$) δ 9.29 (s, 1H), 8.03 (dd, J=7.7, 1.9 Hz, 2H), 7.58-7.43 (m, 5H), 7.25-7.12 (m, 1H), 6.96 (s, 1H), 6.81-6.71 (m, 2H), 4.32 (q, J=2.7 Hz, 2H), 3.83 (t, J=5.4 Hz, 2H), 2.87 (s, 6H), 2.71-2.58 (m, 2H).

Step 2. N4,N4-dimethyl-N1-(6-phenyl-2-tetrahydropyran-4-yl-pyrimidin-4-yl)benzene-1,4-diamine (Compound 16)

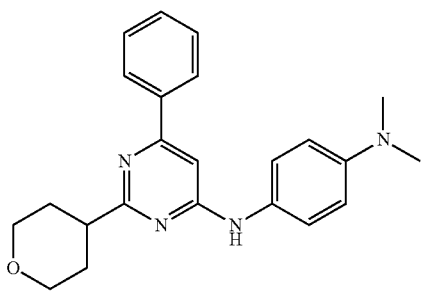 [SMILES: CN(C)c1ccc(Nc2cc(-c3ccccc3)nc(C3CCOCC3)n2)cc1]

Titled compound was obtained using intermediate C.9 (35 mg, 0.09 mmol) following the general procedure reaction D method previously described. Final normal phase purification (cyclohexane/AcOEt from 95/5 to 75/25) afforded pure title compound (27 mg, yield 77%). Rt=1.48 min (analysis method 2); MS (ESI) m/z: 375.5 [M-H]$^+$, [M-H]$^+$ calculated: 375.2. $^1$H NMR (400 MHz, DMSO-d$_6$) δ 9.27 (s, 1H), 8.05-7.91 (m, 2H), 7.63-7.40 (m, 4H), 6.93 (s, 1H), 6.83-6.68 (m, 2H), 3.96 (dt, J=11.4, 2.6 Hz, 2H), 3.48 (td, J=11.1, 3.5 Hz, 2H), 2.93 (dq, J=10.7, 5.8, 5.3 Hz, 1H), 2.88 (s, 5H), 1.96-1.77 (m, 4H).

Example 10. N-(4-methoxyphenyl)-6-phenyl-2-tetrahydropyran-4-yl-pyrimidin-4-amine (Compound 17)

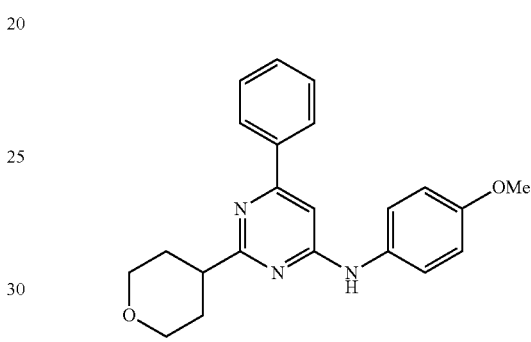

Step 1. 2-(3,6-dihydro-2H-pyran-4-yl)-N-(4-methoxyphenyl)-6-phenyl-pyrimidin-4-amine (Intermediate C.10)

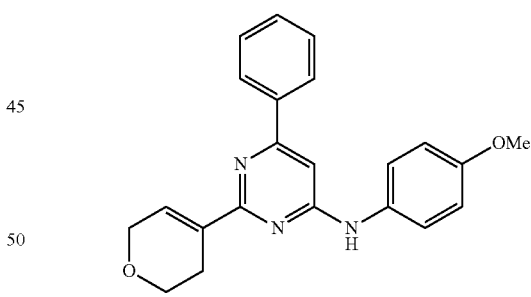

Titled compound was obtained using intermediate B.2 (90 mg, 0.29 mmol) and 3,6-Dihydro-2H-pyran-4-boronic acid pinacol ester (74.3 mg, 0.35 mmol) following the general procedure C previously described. Final normal phase purification (cyclohexane/TBME from 100/0 to 80/20) afforded title compound (44.2 mg, yield 43%). Rt=1.54 min (analysis method 2); MS (ESI) m/z 360.5 [M-H]$^+$, [M-H]$^+$ calculated: 360.2. $^1$H NMR (400 MHz, DMSO-d$_6$) δ 9.45 (s, 1H), 8.12-8.01 (m, 2H), 7.65 (d, J=8.9 Hz, 2H), 7.57-7.45 (m, 5H), 7.01 (s, 1H), 6.98-6.92 (m, 1H), 4.33 (d, J=2.9 Hz, 2H), 3.76-3.72 (m, 5H), 2.71-2.61 (m, 2H).

Step 2. N-(4-methoxyphenyl)-6-phenyl-2-tetrahydropyran-4-yl-pyrimidin-4-amine (Compound 17)

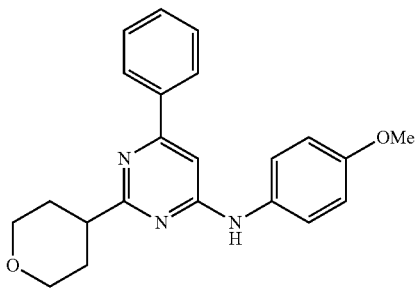 [SMILES: COc1ccc(Nc2cc(-c3ccccc3)nc(C3CCOCC3)n2)cc1]

Titled compound was obtained using intermediate C.10 (42 mg, 0.12 mmol) following the general procedure reaction D method 2 previously described. Final normal phase purification (cyclohexane/TBME from 90/10 to 70/30) afforded pure title compound (16 mg, yield 38%). Rt=1.31 min (analysis method 2); MS (ESI) m/z: 362.5 [M-H]$^+$, [M-H]$^+$ calculated: 362.2. $^1$H NMR (400 MHz, DMSO-d$_6$) δ 9.43 (s, 1H), 8.11-7.88 (m, 2H), 7.63 (d, J=8.5 Hz, 2H), 7.55-7.45 (m, 3H), 6.98 (s, 1H), 6.96-6.90 (m, 2H), 3.96 (ddd, J=11.3, 4.2, 2.3 Hz, 2H), 3.75 (s, 3H), 3.47 (td, J=11.3, 3.0 Hz, 2H), 3.03-2.88 (m, 1H), 1.98-1.77 (m, 4H).

Cell Viability Assay

Cells were seeded at 10,000 cells/well in 96-well plates and incubated for 24 h at 37° C. with 5% CO$_2$. After an overnight incubation, cells were treated with inhibitor (1.25-50 μM) alone or with Cisplatin at 20 μM for 24 hours. The cell viability was determined using the Cell Titer-Glo luminescent cell viability assay kit (Promega, Madison, Wis.), according to the manufacturer's instructions. Luminescence was measured using a DTX 800 microplate reader (Coulter). The half-maximal inhibitory concentration (IC50) values were calculated using the GraphPad Prism software. The assay was done by conducting 3 independent experiments.

The results are illustrated in Table 1

TABLE 1

| Compound number | Structure | Potency |
|---|---|---|
| 1 (ARN12405) | | IC$_{50}$ (alone) 16.4 μM<br>IC$_{50}$ (CisPt) 12.8 μM |
| 2 | | IC$_{50}$ (alone) 14.9 μM<br>IC$_{50}$ (CisPt) 11.5 μM |
| 3 | 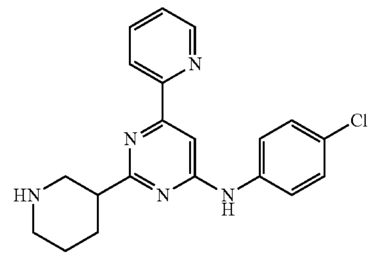 [SMILES: Clc1ccc(Nc2cc(-c3ccccn3)nc(C3CCCNC3)n2)cc1] | IC$_{50}$ (alone) 29.0 μM<br>IC$_{50}$ (CisPt) 38.2 μM |
| 4 | 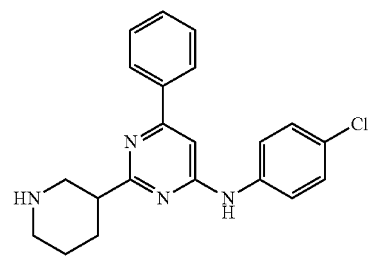 [SMILES: Clc1ccc(Nc2cc(-c3ccccc3)nc(C3CCCNC3)n2)cc1] | IC$_{50}$ (alone) 10.2 μM<br>IC$_{50}$ (CisPt) 7.0 μM |
| 5 | 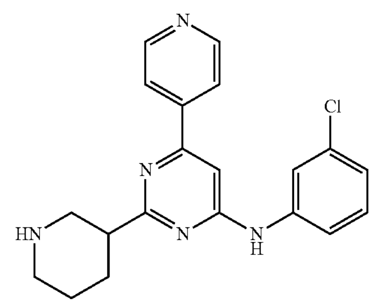 [SMILES: Clc1cccc(Nc2cc(-c3ccncc3)nc(C3CCCNC3)n2)c1] | IC$_{50}$ (alone) 38.3 μM<br>IC$_{50}$ (CisPt) 42.3 μM |
| 6 | 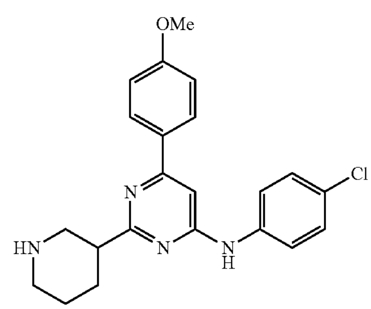 [SMILES: COc1ccc(-c2cc(Nc3ccc(Cl)cc3)nc(C3CCCNC3)n2)cc1] | IC$_{50}$ (alone) 19.7 μM<br>IC$_{50}$ (CisPt) 17.0 μM |
| 7 | 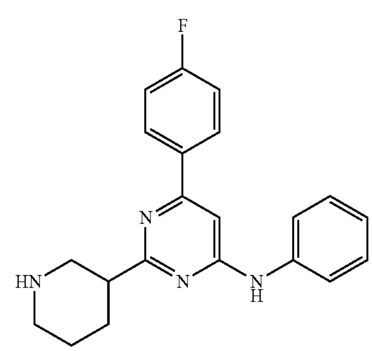 [SMILES: Fc1ccc(-c2cc(Nc3ccccc3)nc(C3CCCNC3)n2)cc1] | IC$_{50}$ (alone) 40.1 μM<br>IC$_{50}$ (CisPt) 32.0 μM |

TABLE 1-continued

| Compound number | Structure | Potency |
|---|---|---|
| 8 | (2-(piperidin-3-yl)-6-phenyl-N-(4-(dimethylamino)phenyl)pyrimidin-4-amine) | IC$_{50}$ (alone) 45.0 μM<br>IC$_{50}$ (CisPt) 31.4 μM |
| 9 | (2-(piperidin-3-yl)-6-phenyl-N-(4-methoxyphenyl)pyrimidin-4-amine) | IC$_{50}$ (alone) >50 μM<br>IC$_{50}$ (CisPt) >50 μM |
| 10 | (2-(piperidin-3-yl)-6-phenyl-N-(3-(dimethylamino)phenyl)pyrimidin-4-amine) | IC$_{50}$ (alone) 45.02 μM<br>IC$_{50}$ (CisPt) 31.4 μM |
| 11 | (2-(piperidin-3-yl)-6-phenyl-N-(3-methoxyphenyl)pyrimidin-4-amine) | IC$_{50}$ (alone) 24.2 μM<br>IC$_{50}$ (CisPt) 27.8 μM |
| 12 | (2-(piperidin-2-yl)-6-phenyl-N-(4-(dimethylamino)phenyl)pyrimidin-4-amine) | IC$_{50}$ (alone) 27.0 μM<br>IC$_{50}$ (CisPt) 86.3 μM |
| 13 | (2-(piperidin-2-yl)-6-phenyl-N-(4-methoxyphenyl)pyrimidin-4-amine) | IC$_{50}$ (alone) 32.5 μM<br>IC$_{50}$ (CisPt) 36.7 μM |
| 14 | (2-(piperidin-4-yl)-6-phenyl-N-(3-(dimethylamino)phenyl)pyrimidin-4-amine) | IC$_{50}$ (alone) 24.8 μM<br>IC$_{50}$ (CisPt) 17.2 μM |
| 15 | (2-(piperidin-4-yl)-6-phenyl-N-(3-methoxyphenyl)pyrimidin-4-amine) | IC$_{50}$ (alone) 38.2 μM<br>IC$_{50}$ (CisPt) 22.2 μM |
| 16 | (2-(tetrahydropyran-4-yl)-6-phenyl-N-(4-(dimethylamino)phenyl)pyrimidin-4-amine) | IC$_{50}$ (alone) >50 μM<br>IC$_{50}$ (CisPt) >50 μM |
| 17 | (2-(tetrahydropyran-4-yl)-6-phenyl-N-(4-methoxyphenyl)pyrimidin-4-amine) | IC$_{50}$ (alone) >50 μM<br>IC$_{50}$ (CisPt) >50 μM |

Flow cytometric analyses for apoptosis Approximately 1×10$^6$ melanoma cells treated with inhibitors for 24 hours and were then trypsinized and washed with PBS, the single-cell suspensions were incubated with Alexa Fluor-Annexin V and propidium iodide (PI) (V13245; Invitrogen) per the manufacturer's protocol and were subjected to flow cytometric analysis. In all cases, cell debris was gated out on the basis of forward scatter and side scatter analysis. Data was analyzed using FlowJo (Ashland, Oreg.). Results are illustrated in FIG. 1, wherein WM3248 melanoma cells were treated with the indicated doses of compound 1 (ARN12405) and apoptosis was measured by flow cytometry using Annexin V and PI.

Cdc42 Activity Assays

Figure 2:
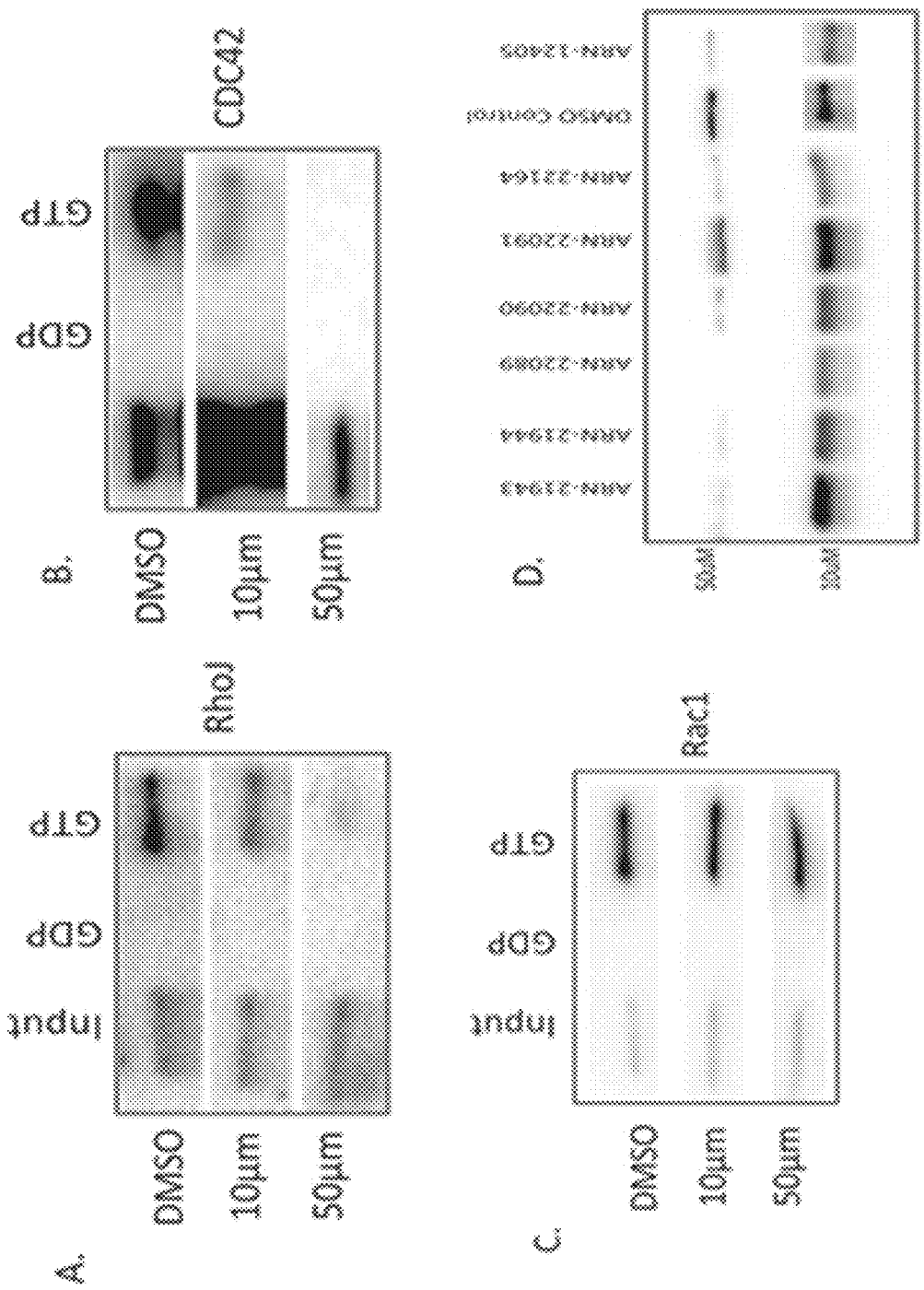
FIG. 2 illustrates block of RhoJ PAK interaction in cell lysates from WM3248 cells incubated with compound 1 (ARN12405) evaluated by SDS PAGE and immunoblotting with a (panel A) RhoJ antibody; (panel B) cdc42 antibody; (panel C) Rac1 antibody. (panel D) Cells treated with compound 1 (ARN12405) at a concentration of 10 μm or 50 μm.

A Cdc42 activation assay was performed according the manufacturer's protocol (Cell Biolabs, San Diego, Calif.). Briefly, cells treated with the inhibitor were lysed and either loaded with GDP or GTPyS. Agarose beads conjugated with the PAK1 PBD domain pulled down Cdc42, Rac1, or RhoJ only when GTP-bound. Lysates were then immunoblotted with indicated Abs. Results are illustrated in FIG. 2. In particular, a Cdc42 activation assay was used to determine whether the inhibitor blocked the ability of RhoJ to interact with PAK coupled beads. Briefly, cells were treated with compound 1 (ARN12405) and cell lysates were prepared and incubated with PAK coupled beads. Immunoprecipitated proteins were subjected to SDS PAGE and immunoblotted with a (A) RhoJ antibody, (B) Cdc42 antibody, (C) Rac1 antibody, (D) Cells were treated with one of a panel of RhoJ interaction inhibitors at a concentration of 10 μm or 50 μm (see FIG. 2, panels A-D). Lysates were prepared, incubated with PAK coupled beads, and immunoprecipitated proteins were immunoblotted with a RhoJ antibody.

The invention claimed is:

1. A compound of formula (I):

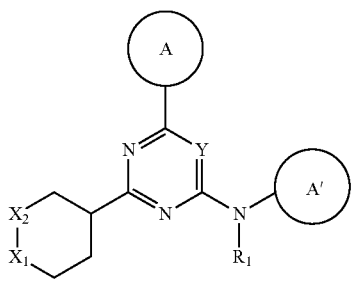

(I)

or a pharmaceutically acceptable salt thereof,
wherein:
A is a 6-membered aromatic ring or a 6-membered heteroaromatic ring, wherein the 6-membered heteroaromatic ring contains 1 or 2 nitrogen atoms, and further wherein the 6-membered aromatic ring or the 6-membered heteroaromatic ring is optionally substituted with 1 substituent selected from the group consisting of halogen, $C_{1-6}$ alkyl, $C_{1-6}$ alkyl(halo), $C_{1-6}$ alkyl(alkoxy), $NH_2$, $NH(C_{1-6}$ alkyl), $N(C_{1-6}$ alkyl)$_2$, and OH;
A' is a 6-membered aromatic ring or a 6-membered heteroaromatic ring, wherein the 6-membered heteroaromatic ring contains 1 or 2 nitrogen atoms, and further wherein the 6-membered aromatic ring or the 6-membered heteroaromatic ring is optionally substituted with 1 substituent selected from the group consisting of halogen, $C_{1-6}$ alkyl, $C_{1-6}$ alkyl(halo), $C_{1-6}$ alkyl(alkoxy), $NH_2$, $NH(C_{1-6}$ alkyl), $N(C_{1-6}$ alkyl)$_2$, and OH;
$X_1$ is —$CH_2$—, —$NR_2$—, or —O—;
$X_2$ is —$CH_2$—, —$NR_2$—, or —O—;
$R_1$ is H or $C_{1-6}$ alkyl;
$R_2$ is H, $C_{1-6}$ alkyl, $C_{1-6}$ alkyl(alkoxy), $C(O)C_{1-6}$ alkyl, or $C(O)C_{1-6}$ alkyl(alkoxy); and
Y is CH;
with the provisos that:
(1) $X_1$ and $X_2$ are not simultaneously —$NR_2$—;
(2) $X_1$ and $X_2$ are not simultaneously —$NR_2$— and —O—; and
(3) $X_1$ and $X_2$ are not simultaneously —O—.

2. The compound according to claim 1, or a pharmaceutically acceptable salt thereof, wherein A is an unsubstituted 6-membered aromatic ring or a 6-membered heteroaromatic ring, wherein the 6-membered heteroaromatic ring contains 1 nitrogen atom.

3. The compound according to claim 1, or a pharmaceutically acceptable salt thereof, wherein A' is a 6-membered aromatic ring, wherein the 6-membered aromatic ring is substituted in the meta position or the para position with 1 $N(CH_3)_2$ substituent.

4. The compound according to claim 1, or a pharmaceutically acceptable salt thereof, wherein:
A is a 6-membered aromatic ring or a 6-membered heteroaromatic ring, wherein the 6-membered heteroaromatic ring contains 1 nitrogen atom, and further wherein the 6-membered aromatic ring or the 6-membered heteroaromatic ring is optionally substituted with 1 substituent selected from the group consisting of halogen, $NH_2$, $NH(C_{1-6}$ alkyl), and $N(C_{1-6}$ alkyl)$_2$;
A' is a 6-membered aromatic ring or a 6-membered heteroaromatic ring, wherein the 6-membered heteroaromatic ring contains 1 nitrogen atom, and further wherein the 6-membered aromatic ring or the 6-membered heteroaromatic ring is optionally substituted with 1 substituent selected from the group consisting of halogen, $NH_2$, $NH(C_{1-6}$ alkyl), and $N(C_{1-6}$ alkyl)$_2$;
$R_1$ is H; and
$R_2$ is H.

5. The compound according to claim 1, or a pharmaceutically acceptable salt thereof, wherein:
A is a 6-membered aromatic ring or a 6-membered heteroaromatic ring, wherein the 6-membered heteroaromatic ring contains 1 nitrogen atom in position 2 or position 3, and further wherein the 6-membered aromatic ring is optionally substituted with 1 halogen substituent;
A' is a 6-membered aromatic ring, wherein the 6-membered aromatic ring is optionally substituted in the meta position or the para position with 1 substituent selected from the group consisting of halogen and $N(C_{1-6}$ alkyl)$_2$;
$X_1$ is —$CH_2$—, —$NR_2$—, or —O—;
$X_2$ is —$CH_2$— or —$NR_2$—;
$R_1$ is H; and
$R_2$ is H.

6. The compound according to claim 1, wherein the compound is selected from the group consisting of:

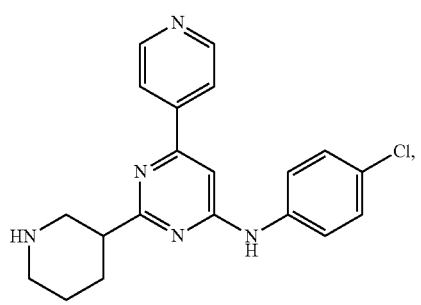

1

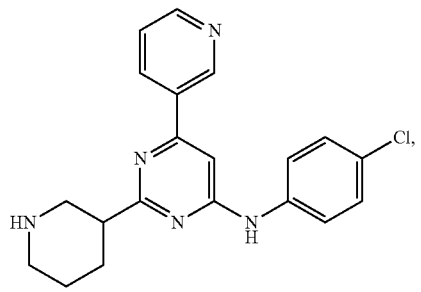

2

3
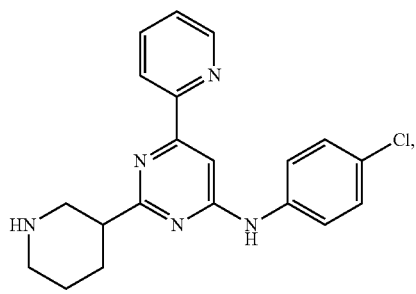

4
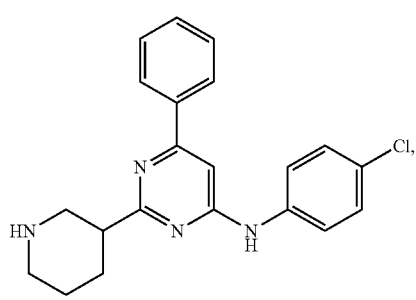

5
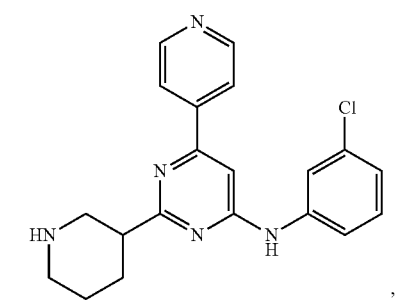

7
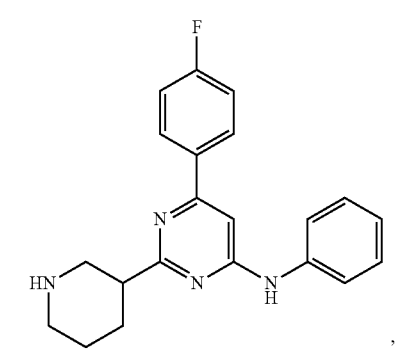

8
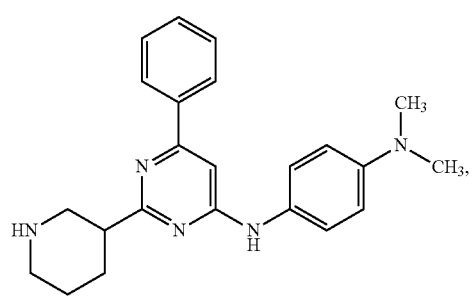

10
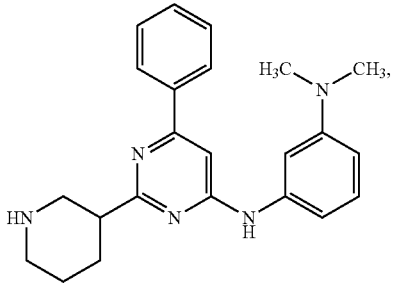

12

14

16 or a pharmaceutically acceptable salt thereof.

7. A medicament comprising the compound according to claim 1, or a pharmaceutically acceptable salt thereof.

8. The medicament according to claim 7, wherein the medicament further comprises at least one pharmaceutically acceptable excipient.

9. A pharmaceutical composition comprising at least one pharmaceutically acceptable excipient and the compound according to claim 1, or a pharmaceutically acceptable salt thereof.

10. The pharmaceutical composition according to claim 9, wherein the pharmaceutical composition further comprises a chemotherapeutic agent selected from the group consisting of carboplatin, cisplatin, dacarbazine, nedaplatin, oxaliplatin, satraplatin, temozolamide, and triplatin tetranitrate.

11. The pharmaceutical composition according to claim 10, wherein the pharmaceutical composition is administered separately, simultaneously, or sequentially.

12. A method for inhibiting RhoJ activity or cell division control protein 42 homolog-guanosine triphosphate hydrolyzing protein activity in a subject, comprising administering to the subject in need thereof a therapeutically effective amount of the compound according to claim 1, or a pharmaceutically acceptable salt thereof.

13. The method according to claim 12, wherein the subject has a disease or disorder selected from the group consisting of a metastatic neoplastic disease, a primary neoplastic disease, and a pre-malignant condition.

14. The method according to claim 13, wherein the metastatic neoplastic disease, the primary neoplastic disease, or the pre-malignant condition is selected from the group consisting of a benign tumor, a cancer, a cancer metastasis, a cardiomyopathy, a dysplasia, a hyperplasia, a hyperproliferative disorder, a metaplasia, and a retinal disorder.

15. The method according to claim 14, wherein the cancer is melanoma.

16. A method for inhibiting RhoJ activity or cell division control protein 42 homolog-guanosine triphosphate hydrolyzing protein activity in a subject, comprising administering to the subject in need thereof a therapeutically effective amount of the pharmaceutical composition according to claim 9.

17. The method according to claim 16, wherein the subject has a disease or disorder selected from the group consisting of a metastatic neoplastic disease, a primary neoplastic disease, and a pre-malignant condition.

18. The method according to claim 17, wherein the metastatic neoplastic disease, the primary neoplastic disease, or the pre-malignant condition is selected from the group consisting of a benign tumor, a cancer, a cancer metastasis, a cardiomyopathy, a dysplasia, a hyperplasia, a hyperproliferative disorder, a metaplasia, and a retinal disorder.

19. The method according to claim 18, wherein the cancer is melanoma.

20. A compound selected from the group consisting of:

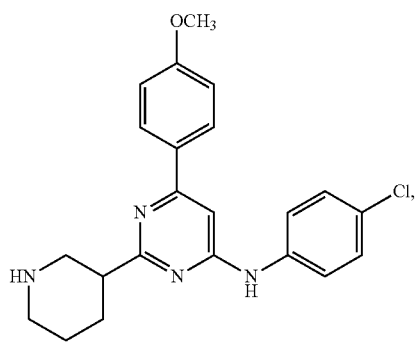

6

-continued

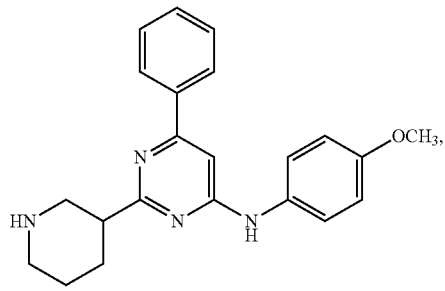

9

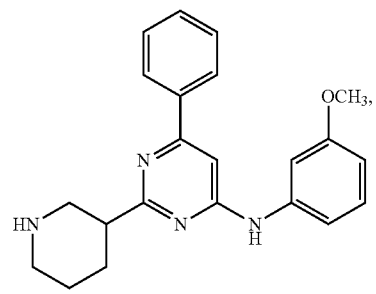

11

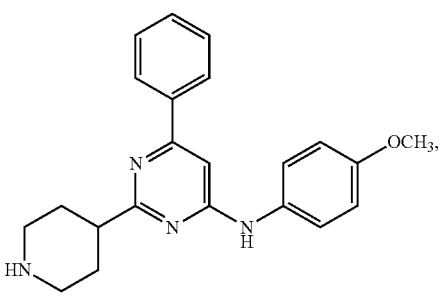

13

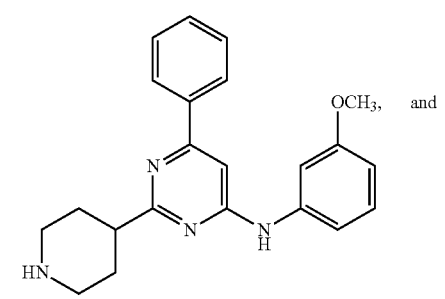

15

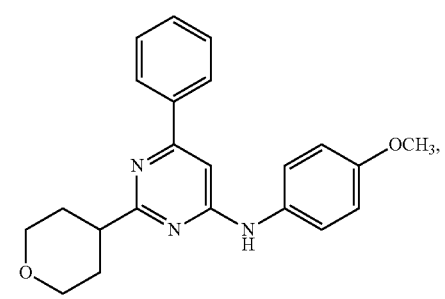

17 or a pharmaceutically acceptable salt thereof.

* * * * *